US007094756B2

(12) United States Patent
Beyaert et al.

(10) Patent No.: US 7,094,756 B2
(45) Date of Patent: Aug. 22, 2006

(54) ABIN-MEDIATED HEPATITIS PROTECTION

(75) Inventors: Rudi Beyaert, Zingem (BE); Ben Wielockx, Ghent (BE); Sofie Van Huffel, Singapore (SG); Filip Delaei, Reet (BE); Claude Libert, Oudenaarde (BE)

(73) Assignee: Vlaams Interuniversitair Instituut Voor Biotechnologie VZW, Zwijnaarde (BE)

( * ) Notice: Subject to any disclaimer, the term of this patent is extended or adjusted under 35 U.S.C. 154(b) by 0 days.

(21) Appl. No.: 10/741,923

(22) Filed: Dec. 19, 2003

(65) Prior Publication Data
US 2004/0136978 A1 Jul. 15, 2004

Related U.S. Application Data

(63) Continuation of application No. PCT/EP02/07154, filed on Jun. 20, 2002.

(30) Foreign Application Priority Data
Jun. 22, 2001 (EP) ................... 01202414

(51) Int. Cl.
*A61K 38/00* (2006.01)
(52) U.S. Cl. ........................ 514/12
(58) Field of Classification Search ............... 530/350; 514/12
See application file for complete search history.

(56) References Cited

U.S. PATENT DOCUMENTS

| 4,186,183 A | 1/1980 | Steck et al. |
| 4,217,344 A | 8/1980 | Venlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |

FOREIGN PATENT DOCUMENTS

| WO | WO 91/16024 | 10/1991 |
| WO | WO 91/17424 | 11/1991 |
| WO | WO 93/24641 | 12/1993 |
| WO | WO 97/37016 | 10/1997 |
| WO | WO 99/57133 | * 11/1999 |
| WO | WO 03/000280 A2 | 1/2003 |

OTHER PUBLICATIONS

Kono et al., NADPH oxidase-derived free radicals are key oxidants in alchohol-induced disease, J. Clin. Invest., (2000), 106, p. 867-872.*
De Valck et al., "A20, an inhibitor of cell death, self-associates by its zinc finger domain," 384 FEBS Letters 61-64 (1996).
Fukushi, M., Homosapiens mRNA for HIV-I, Nef-associated factor 1 beta (Nafl bets),: Emhum Database Entry HSA011896, Accession No. AJ011896, Oct. 14, 1998, XP002124741.
Fukushi, M., et al., "NAF1 alpha protein (KIAA0113 protein)," Trembl Database Entry A15025, Accession No. Q15025, Nov. 1, 1996, XP02124740.
Hendrick, B.D., et al., "An X-linked homologue of the autosomal imprinted gene NF127 escapes X chromosome inactivation," Emhum Database Entry HS4131510; Accession No. U41315, May 19, 1996, XP002125387.
Heyninck et al, "The Zinc Finger Protein A20 Inhibits TNF-induced NF-kB-dependent Gene Expression by interfering with an RIP- or TRAF2-mediated Transactivation Signal and Directly Binds to a Novel NF-kB-inhibiting Protein ABIN," 145 The Journal of Cell Biology 1471-1482 (1999).
Miyajima, N., et al., "Human mRNA for KIAA 0133 gene, partial coding sequence," Emhum Databse Entry HSORFA2, Accession No. D30755, May 21, 1994, XP002124739.
Nomura et al., "mRNA for ORF, partial CDS (fragment)," Trhum Database Entry Q15025; Nov. 1, 1996, Accession No. Q15025, XP002080989.
Song et al., "The tumor necrosis factor-inducible zinc finger protein A20 interacts with TRAF1/TRAF2 and inhibits NF-kB activation," 93 Proc. Natl. Acad. Sci. USA 6721-6725 (1996).
Yen, R.W.C., et al., "DNA-methyltransferase," Swissprot Database Entry MTDM_Human; May 1, 1992, Accession No. P26358, XP002080990.
PCT International Preliminary Examination Report, PCT/BE99/00055, DATED Aug. 10, 2000, 8 pages.
PCT International Search Report, PCT/BE99/00055, dated Dec. 29, 1999, 3 pages.
Fukushi et al., (Nov. 1, 1996) Acc. No. Q15025, SPTREMBL_17 database, GenCore Version 4.5, Accessed May 8, 2002.

(Continued)

*Primary Examiner*—Karen Cochrane Carlson
*Assistant Examiner*—Agnes Rooke
(74) *Attorney, Agent, or Firm*—TraskBritt

(57) ABSTRACT

The present invention relates to the use of the A20-binding inhibitor of NF-κB activation (ABIN), or a functional fragment or variant thereof to protect against TNF-induced liver failure, such as viral hepatitis and alcoholic liver disease. More particularly, it relates to the prevention of the toxic effects of said diseases, including lethality, by overexpressing ABIN.

2 Claims, 6 Drawing Sheets

OTHER PUBLICATIONS

Gupta, et al. (Mar. 1, 2001) Acc. No. Q9HIJ3, SPTREMBL_17, GenCore Version 4.5, Accessed May 8, 2002.

Beyaert et al., A20 and A20-Binding Proteins as Cellular Inhibitors of Nuclear Factor-kB-Dedpendant Gene Expression and Apoptosis, Biochemical Pharmacology, 2000, pp. 1143-1151, vol. 60.

Baldwin, Jr. et al., The transcription factor NF-kB and human disease, The Journal of Clinical Investigation, Jan. 2001, pp. 3-6, Jan. 2001, vol. 107, No. 1.

Ghosh et al., Missing Pieces in the NF-kB Puzzle, Cell, Apr. 2002, pp. S81-S96, vol. 109.

Heyninck et al., Structure-function analysis of the A20-binding inhibitor of NF-kB activation, ABIN-I, FEBS Letters, 2003, pp. 135-140, vol. 536.

Ngo et al., Computational Complexity, Protein Structure Prediction, and the Levinthal Paradox, The Protein Folding Problem and Tertiary Structure Prediction, 1994, pp. 491-495.

Yamamoto et al., Therapeutic potential of inhibition of the NF-kB pathway in the treatment of inflammation and cancer, The Journal of Clinical Investigation, Jan. 2001, pp. 135-142, vol. 107, No. 2.

Zhang et al., Environment-dependent residue contact energies for proteins, PNAS, Mar. 14, 2000, pp. 2550-2555, vol. 97, No. 6.

PCT International Search Report, PCT/EP02/07154, dated Dec. 16, 2002.

PCT International Preliminary Examination Report, PCT/EP02/07154, Apr. 3, 2003, 7 pages.

Kaplowitz, Neil, "Hepatology Highlights;" Hepatology, Aug. 2005, pp. 247-248, vol. 42, No. 2.

Wullaert et al., "Adenoviral Gene Transfer of ABIN-1 Protects Mice from TNF/Galactosamine-Induced Acute Liver Failure and Lethality," Hepatology, Aug. 2005, pp. 381-389, vol. 42, No. 2.

\* cited by examiner

ABIN-MEDIATED HEPATITIS PROTECTION

CROSS-REFERENCE TO RELATED APPLICATION

This application is a continuation of PCT International Patent Application No. PCT/EP02/07154, filed on Jun. 20, 2002, designating the United States of America, and published, in English, as PCT International Publication No. WO 03/000280 A2 on Jan. 3, 2003, the contents of the entirety of which is incorporated by this reference. This application claims foreign priority to European Patent Office (EPO) 01202414.7 filed on Jun. 22, 2001.

TECHNICAL FIELD

The present invention relates generally to biotechnology, and, more specifically, to the use of the A20-binding inhibitor of NF-kappaB (NF-κB) activation (ABIN) to protect against TNF-induced liver failure, such as viral hepatitis and alcoholic liver disease. More particularly, it relates to the prevention of the toxic effects of such diseases, including lethality, by over-expressing ABIN.

BACKGROUND

Acute liver failure is a clinical syndrome that results from massive necrosis and apoptosis of liver cells leading to hepatic encephalopathy and severe impairement of hepatic function. It is caused by different kinds of diseases, such as viral hepatitis (A, B, C, . . . ), drugs, intoxication, autoimmune hepatitis, etc. Many studies have shown that TNF plays a central role in liver disease. TNF is produced mainly by activated macrophages but is also produced in smaller amounts by several other cell types. TNF exerts a variety of effects on different cell types and is implicated as an important mediator in various physiological and pathophysiological conditions. In addition, it has become clear that TNF is an important mediator of apoptosis (programmed cell death).

TNF was originally identified by its capacity to induce hemorrhagic necrosis of tumors in mice. Attempts to use TNF for systemic anti-cancer therapy have failed due to the appearance of severe side effects before therapeutic doses could be reached. One of the side effects of TNF treatment was an elevation in serum levels of transaminases and bilirubin levels, indicating a direct cytotoxic effect of TNF on human hepatocytes. Subsequent studies have shown that TNF may be involved in viral hepatitis, alcoholic liver disease, and fulminant hepatic failure (Muto et al., 1988; Bird et al., 1990; Gonzalez-Amaro et al., 1994; Diehl et al., 1994; Larrea et al., 1996). TNF serum levels are clearly elevated in patients with fulminant hepatitis (Muto et al., 1988). In addition, it was found that serum TNF levels were significantly higher in patients who died than in patients who survived (Bird et al., 1990).

A role for TNF in the pathogenesis of chronic hepatitis B and C viral infection has been suggested. Both viruses induce TNF expression in human liver and human hepatoma cell lines (Gonzalez-Amaro et al., 1994). Patients with chronic hepatitis B have elevated plasma TNF levels, and their peripheral blood mononuclear cells show enhanced TNF production in vitro. In addition, in chronic hepatitis B-infected patients undergoing interferon treatment, a massive increase in spontaneous TNF production by blood mononuclear cells was observed at the time of successful antigen seroconversion (Diehl et al., 1994), suggesting that the increased TNF levels may be involved in hepatitis B virus clearance. Furthermore, the serum levels of soluble TNF-R1 and TNF-R2 are significantly elevated in chronic hepatitis B infection. The serum levels of soluble TNF-R2 correlate closely with the extent of inflammation and hepatocyte death in the liver. During interferon therapy, the response and the increase in transaminases are associated with an increase in soluble TNF-R2 serum levels. For hepatitis C patients, interferon treatment clears the virus and reduces TNF levels to normal in responsive patients (Larrea et al., 1996). Interestingly, pretreatment levels of TNF were higher in unresponsive compared with responsive patients (Larrea et al., 1996). Hepatitis C proteins interact with the TNF receptor, although whether this interaction promotes or prevents apoptosis is not clear (Ray et al., 1998). Recently, an interaction between hepatitis C virus NS5A protein and the TNF-receptor-associated proteins TRADD and TRAF2 has been shown (Majumder et al., 2002; Park et al., 2002). Park and coworkers showed that NS5A impairs TNF-mediated hepatic apoptosis by preventing the association between TRADD and FADD. Moreover, both groups also showed that NS5A prevents TRADD and TRAF2-mediated NF-κB activation.

TNF serum levels are increased in patients with alcoholic hepatitis, and the levels correlate inversely with patient survival. TNF concentrations were significantly higher in patients who did not survive an episode of acute alcoholic hepatitis (Bird et al., 1990). Monocytes isolated from patients with alcoholic hepatitis spontaneously produced higher amounts of TNF compared with healthy controls. Monocytes derived from patients with alcoholic hepatitis also produced significantly more TNF in response to LPS than normal monocytes. Several hypotheses have been developed to explain increased TNF levels in patients with chronic ethanol exposure. Chronic ethanol feeding increases the permeability of the gut to bacterial products such as LPS, potentially inducing TNF production in macrophages (McClain, 1991). In addition, studies investigating the promoter polymorphism in patients with alcoholic steatohepatitis indicated that patients with alcoholic steatohepatitis had a mutation in the TNF promoter that increases its activity (Grove et al., 1997). Thus genetic factors may be involved in the increased TNF production in patients with alcoholic hepatitis.

The role of TNF in liver injury has been studied in several animal models. By using neutralizing anti-TNF antibodies or knockout mice for TNF, TNF-R1, or TNF-R2, it has become evident that TNF triggers apoptosis and/or necrosis of hepatocytes in vivo. In different animal models of liver injury, TNF plays a central or an additive role in the pathogenesis of acute liver injury. Here we used the TNF/Galactosamine (GalN) model. In this model, TNF is administered in combination with D-(+)-galactosamine (GalN), a hepatotoxin, that selectively blocks transcription in hepatocytes by depleting uridine nucleotides (Dekker and Keppler, 1974), inducing lethality, activation of caspases and subsequent hepatocyte apoptosis (Leist et al., 1995; Van Molle et al., 1999; Tiegs et al., 1989). TNF-R1 knockout mice are resistant to TNF/GalN treatment, demonstrating the essential role of TNF-R1 in this apoptosis model (Leist et al., 1995). The sensitizing effect of GalN suggests that the transcriptional block induced by GalN directly inhibits synthesis of anti-apoptotic proteins. Recently, the transcription factor NF-κB has been shown to regulate the expression of a number of anti-apoptotic proteins.

NF-κB is an essential transcription factor that is ubiquitously expressed in all cell types and whose activity is modulated by a wide range of inducers, including cytokines and bacterial or viral products. Many of the NF-κB responsive genes play a key role in the regulation of inflammatory and immune responses. Deregulation of NF-κB activity is often observed in several chronic inflammatory diseases such as rheumatoid arthritis, asthma and inflammatory bowel disease, as well as in acute diseases such as septic shock. Furthermore, NF-κB serves to protect against apoptosis and supports cell cycle progression. The first indication that NF-κB activation may modulate hepatocyte responses relevant to liver injury was the finding that knockout mice deficient in the p65/Rel-A subunit of NF-κB were nonviable because of massive hepatocyte apoptosis during embryogenesis (Beg et al., 1995). Recent reports from several laboratories have now demonstrated that NF-κB activation regulates hepatocyte proliferation and apoptosis in vivo and in vitro. In rats subjected to partial hepatectomy, inhibition of NF-κB activation impaired subsequent liver regeneration and triggered hepatocyte apoptosis (Iimuro et al, 1998). These findings suggest a critical role for NF-κB activation in hepatocytes following a mitogenic stimulus, although the mechanism by which inhibition of NF-κB activity blocked proliferation is unclear. Apoptosis may have resulted from a cell cycle block or from sensitization to TNF produced following partial hepatectomy. An essential role for NF-κB activation during hepatocyte proliferation is also supported by the finding that inhibition of NF-κB activity resulted in apoptosis in an exponentially growing murine hepatocyte cell line (Bellas et al., 1997). However, other studies in confluent rat hepatocyte cultures have demonstrated that NF-κB inhibition by itself did not result in cell death (Xu et al., 1998). In these cells, NF-κB inhibition did convert the hepatocellular response to the mitogenic stimulus of TNF from proliferation to one of apoptosis (Xu et al., 1998). The mechanism by which NF-κB inactivation triggered TNF-induced apoptosis in these studies involved activation of the caspase cascade, and cell death could be prevented by caspase inhibition or NO (Xu et al., 1998).

The NF-κB-dependent gene product(s) that protects hepatocytes against TNF-induced injury remains to be identified. Possible candidate genes are iNOS and interleukin-6, since they are regulated by NF-κB and their gene products may have hepatoprotective effects. It also remains to be determined whether NF-κB activation inhibits hepatotoxicity from injurious agents other than TNF. In the hepatoma cell line Hep G2, treatment with a nontoxic concentration of the superoxide generator menadione protected against subsequent toxic doses of menadione or $H_2O_2$ by an NF-κB-dependent mechanism (Chen and Cederbaum, 1997). However, studies in a rat hepatocyte cell line demonstrated that, although $H_2O_2$ and copper induced NF-κB activation and caused apoptosis at toxic concentrations, inhibition of NF-κB activity did not sensitize the cells to death from $H_2O_2$ or copper (Xu et al., 1998). NF-κB activation may therefore stimulate a defense mechanism specific for the TNF death pathway.

The possibility that NF-κB activation in hepatocytes is protective following liver injury points to the complexity of events following global activation of NF-κB in all cell types in the liver. After a toxic stimulus, it is known that activation of NF-κB in hepatic macrophages results in the production of injurious products such as cytokines and reactive oxygen intermediates. Inhibition of hepatic NF-κB activation was therefore viewed as a potential therapy for liver injury. It now appears that NF-κB signalling represents a problematic therapeutic target, since blanket inhibition of hepatic NF-κB activation may lead to both beneficial and detrimental effects.

Recently, considerable progress has been made in understanding the details of signalling pathways that regulate and mediate NF-κB activation in response to TNF and IL-1. These cytokines act by binding to specific cell surface receptors, which in turn initiate the recruitment of a number of specific adaptor proteins, and the activation of a kinase complex that phosphorylates the NF-κB inhibitor IκB. The latter retains NF-κB in the cytoplasm in an inactive dimeric form. Once phosphorylated, IκB is marked for ubiquitination and subsequent degradation by the proteasome, allowing the nuclear translocation of NF-κB. Whereas members of the IκB family have been well studied as direct inhibitors of NF-κB, a number of other proteins have been reported to negatively regulate NF-κB-dependent gene expression. We and others have previously shown that the zinc finger protein A20 is a potent inhibitor of NF-κB activation in response to TNF, IL-1, LPS and CD-40 (reviewed in Beyaert et al., 2000). In addition, A20 also exerts an anti-apoptotic function in a number of cell lines. A20 is only expressed upon NF-κB activation, and is involved in the negative feedback regulation of NF-κB activation. A20-deficient mice were recently shown to be defective in the termination of NF-κB activation, leading to strong inflammatory responses and cachexia (Lee et al., 2000). The underlying mechanisms responsible for the inhibition of NF-κB-dependent gene expression by A20 is still unclear. A20 interacts with the IκB kinase complex, as well as with TRAF2 and TRAF6, which are part of the IκB kinase activation cascade initiated by TNF and IL-1/LPS, respectively. In addition, three novel A20-binding proteins (ABIN, ABIN-2 and ABIN-3) were recently isolated. Upon overexpression in cell lines, these proteins were shown to inhibit NF-κB-dependent gene expression in response to TNF or IL-1 (Beyaert et al., 2000; Heyninck et al., 1999; Van Huffel et al., 2001, Van Huffel et al., unpublished; AJ320534).

DISCLOSURE OF THE INVENTION

The present invention relates to the surprising finding that overexpression of ABIN prevents TNF-induced lethal hepatitis in mice.

The invention includes methods of treating TNF-induced liver failure in a subject (e.g., a mammal such as a human). The TNF-induced liver failure can be of, for example, viral hepatitis, fulminant hepatitis and/or alcoholic liver disease origin.

In one such method, the method comprises administering isolated ABIN, or a functional fragment or variant thereof to the subject. The ABIN can comprises the consensus amino acid sequence depicted in SEQ ID NO:4, SEQ ID NO:5, or SEQ ID NO:4 and SEQ ID NO:5. An exemplary functional fragment of ABIN is a fragment comprising the amino acid sequence depicted in SEQ ID NO:3 that interacts with protein A20 or a fragment comprising amino acids 420–647 of SEQ ID NO:2 that interacts with protein A20. An exemplary variant of ABIN may be selected from the group consisting of Nafl alpha protein, Nafl beta protein, and virion-associated nuclear shuttling protein.

In another embodiment, the invention includes a method of treating TNF-induced liver failure in a subject, the method comprising administering to the subject a nucleotide sequence encoding ABIN, or a functional fragment or variant thereof. The nucleotide sequence may be administered as a gene therapy vector.

In another embodiment, the invention includes a method of treating TNF-induced liver failure in a subject, the method comprising administering an ABIN inducing and/or activating compound (e.g., PHA) to the subject.

DETAILED DESCRIPTION OF THE INVENTION

Figure 1:
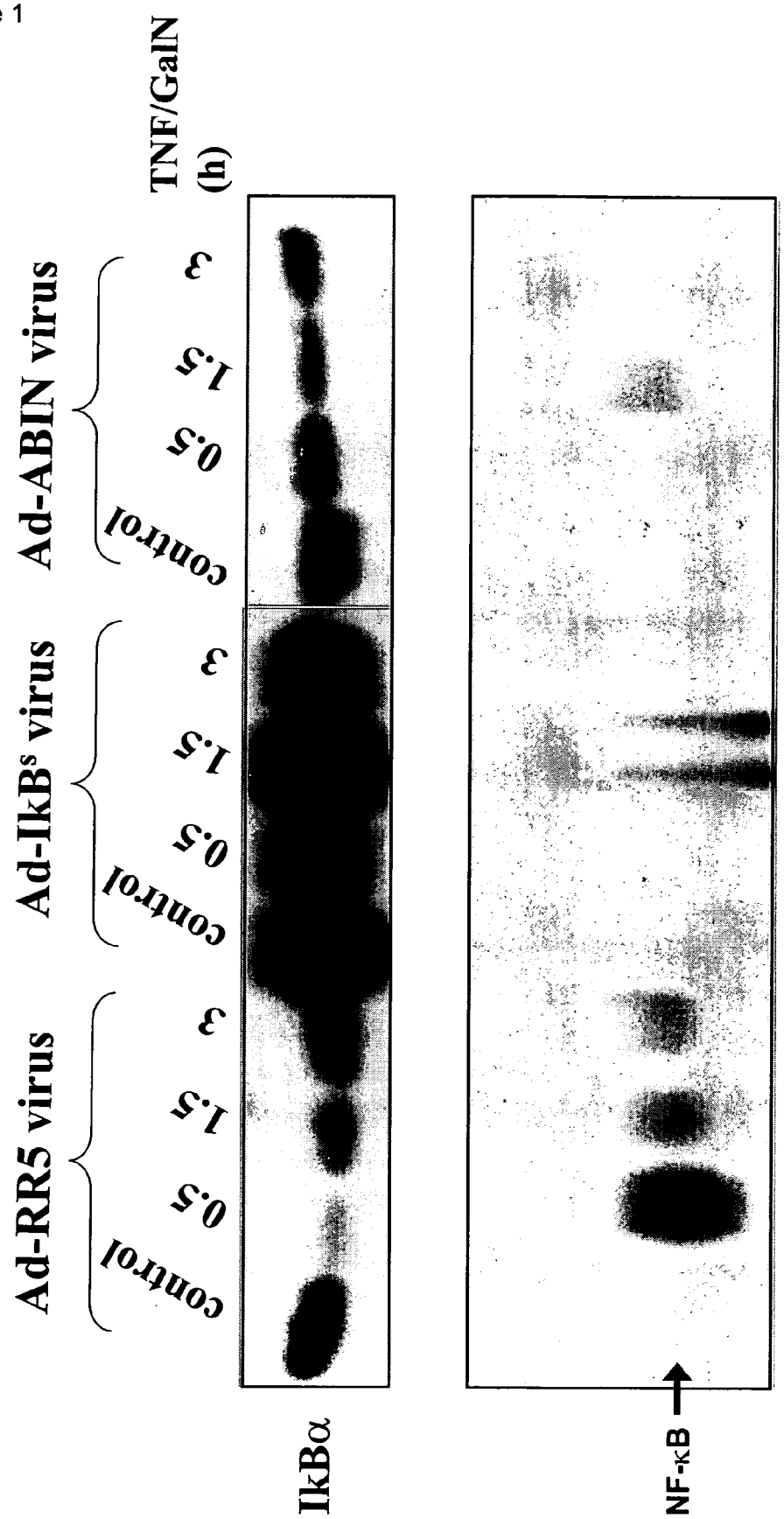
FIG. 1: Effect of AdABIN on TNF/GalN-stimulated degradation of IκB (upper panel) and DNA binding of NF-κB (lower panel) in vivo. Mice were injected (i.v.) with $2.5 \times 10^9$ pfu Ad-ABIN, Ad-IκB$^S$ (=IκB super-repressor), or AdRR5 (=empty virus control), and challenged after three days by injection with a lethal dosage of TNF (0.3 μg)/GalN (20 mg) diluted in PBS. PBS as such served as a control. Different times after TNF/GalN treatment, mice were killed and liver homogenates were prepared. IκBα expression was analyzed by SDS-PAGE and immunoblotting with polyclonal anti-IκBα antibody (upper panel). NF-κB DNA binding was analyzed by incubating 10 μg nuclear extract with radiolabeled probe and run on a native gel. Binding of NF-κB to the DNA probe was revealed by exposure to an X-ray film (lower panel).

A first aspect of the invention is the use of ABIN, as represented in SEQ ID NO:2 of the accompanying and incorporated by this reference SEQUENCE LISTING, or a functional fragment or variant thereof for the preparation of a medicament for the treatment of TNF-induced liver failure. The term "ABIN" relates to ABIN, ABIN-2 and ABIN-3 as disclosed in Beyaert et al., 2000; Heyninck et al., 1999; Van Huffel et al., 2001, Van Huffel et al. (unpublished; AJ320534) and PCT International Publication No. WO 99/57133. More specifically, the term ABIN relates to any polypeptide that comprises the consensus amino acid sequence(s) as depicted in SEQ ID NO:4 and/or SEQ ID NO:5 which are also disclosed in PCT International Publication No. WO 99/57133 that is hereby incorporated by reference. A second aspect of the invention is the use of a nucleotide sequence encoding ABIN, as represented in SEQ ID NO:1, or for a functional fragment or a variant thereof, for the manufacture of a medicament for the treatment of TNF-induced liver failure. A functional fragment of ABIN is a polypeptide that is still able to interact with protein A20 and/or capable of modulating NF-κB activation. Preferably, the modulation is an inhibition of NF-κB activation. Functional fragments are, as a non limiting example, fragments that comprise at least amino acids 420–647 of SEQ ID NO:2, preferably at least amino acids 390–647, more preferably at least 54–647 (SEQ ID NO:3). Preferentially, the fragment is essentially consisting of at least amino acids 420–647 of SEQ ID NO:2, preferably at least amino acids 390–647, more preferably at least 54–647 (SEQ ID NO:3). Variants are polypeptides with at least 65% identity on amino acid level, preferably 70% identity, as measured by BLAST (Altschul et al., 1997). Variants have common characteristics, such as biological activity, immunological reactivity, conformation etc. As a non-limiting example, Naf1 alpha protein (AJO11895), Naf1 beta protein (AJO11896) and virion-associated nuclear shuttling protein (AY012155) are considered as variants.

A further aspect is the use of an ABIN inducing and/or activating compound for the preparation of a medicament for the treatment of TNF-induced liver failure. As a non-limiting example, phytohemagglutinin (PHA) is an ABIN inducing compound (Gupta et al., 2000). In the case of ABIN-3, LPS induces expression of this protein in THP1 monocytes.

The TNF-induced liver failure is, as a non-limiting example, viral hepatitis such as hepatitis A, B or C, fulminant hepatitis and/or alcoholic liver disease. In case a nucleic acid is used, the medicament is preferably intended for delivery of the nucleic acid into the cell, in a gene therapy treatment. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. Methods of non-viral delivery of nucleic acids include lipofection, microinjection, biolistics, virosomes, liposomes, immunoliposomes, polycation or lipid: nucleic acid conjugates, naked DNA, artificial virions, and agent-enhanced uptake of DNA. Lipofection is described in, for example, U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Flegner, PCT International Publication No. WO 91/17424, PCT International Publication No. WO 91/16024. Delivery can be to cells (ex vivo administration) or target tissues (in vivo administration). The preparation of lipid: nucleic acid complexes, including targeted liposomes such as immunolipid complexes, is well known to one of skill in the art (see, e.g., Crystal, 1995; Blaese et al., 1995; Behr, 1994; Remy et al., 1994; Gao and Huang, 1995; U.S. Pat. Nos. 4,186,183, 4,217,344, 4,235,871, 4,261,975, 4,485,054, 4,501,728, 4,774,085, 4,837,028, and 4,946,787). The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long-term expression of the inserted transgene. Additionally, high transduction efficiencies have been observed in many different cell types and target tissues.

In cases where transient expression of the nucleic acid is preferred, adenoviral based systems, including replication-deficient adenoviral vectors are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors, including recombinant adeno-associated virus vectors are also used to transduce cells with target nucleic acids, e.g., in the in vitro production of nucleic acids and peptides, and for in vivo and ex vivo gene therapy procedures (see, e.g., U.S. Pat. No. 4,797,368; PCT International Publication No. WO 93/24641; Kotin, 1994; Muzyczka. The construction of recombinant AAV vectors is described in a number of publications, including U.S. Pat. No. 5,173,414; Hermonat & Muzyczka, 1984; Samulski et al., 1989).

Gene therapy vectors can be delivered in vivo by administration to an individual patient, typically by systemic administration (e.g., intravenous, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, and tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfections are well known to those of skill in the art (see, e.g., Freshney et al., 1994) and the references cited therein for a discussion of how to isolate and culture cells from patients).

In a further embodiment, the invention provides a method for the production or manufacture of a medicament or a pharmaceutical composition comprising ABIN or a functional fragment or variant thereof and further more mixing the polypeptide with a pharmaceutically acceptable carrier.

The administration of the pharmaceutical composition may be by way of oral, inhaled or parenteral administration. The active compound may be administered alone or preferably formulated as a pharmaceutical composition. A unit dose will normally contain 0.01 to 50 mg for example 0.01 to 10 mg, or 0.05 to 2 mg of compound or a pharmaceutically acceptable salt thereof. Unit doses will normally be administered once or more than once a day, for example 2, 3, or 4 times a day, more usually 1 to 3 times a day, such that the total daily dose is normally in the range of 0.0001 to 1 mg/kg; thus a suitable total daily dose for a 70 kg adult is 0.01 to 50 mg, for example 0.01 to 10 mg or more usually 0.05 to 10 mg. It is greatly preferred that the compound or a pharmaceutically acceptable salt thereof is administered in the form of a unit-dose composition, such as a unit dose oral, parenteral, or inhaled composition. Such compositions are prepared by admixture and are suitably adapted for oral, inhaled or parenteral administration, and as such may be in the form of tablets, capsules, oral liquid preparations, powders, granules, lozenges, reconstitutable powders, injectable and infusable solutions or suspensions or suppositories or aerosols. Tablets and capsules for oral administration are usually presented in a unit dose, and contain conventional excipients such as binding agents, fillers, diluents, tabletting agents, lubricants, disintegrants, colorants, flavourings, and wetting agents. The tablets may be coated according to well-known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate. These solid oral compositions may be prepared by conventional methods of blending, filling, tabletting or the like. Repeated blending operations may be used to distribute the active agent throughout those compositions employing large quantities of fillers. Such operations are, of course, conventional in the art. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating. Preferably, compositions for inhalation are presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns, for example between 1 and 5 microns, such as between 2 and 5 microns. A favored inhaled dose will be in the range of 0.05 to 2 mg, for example 0.05 to 0.5 mg, 0.1 to 1 mg or 0.5 to 2 mg. For parenteral administration, fluid unit dose forms are prepared containing a compound of the present invention and a sterile vehicle. The active compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum. Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound. Where appropriate, small amounts of bronchodilators for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included. As is common practice, the compositions will usually be accompanied by written or printed directions for use in the medical treatment concerned.

With regard to the protein transduction with ABIN or ABIN-fragments into target cells, it has been shown that a series of small protein domains, termed protein transduction domains (PTDs), cross biological membranes efficiently and independently of transporters or specific receptors, and promote the delivery of peptides and proteins into cells. For example, the TAT protein from human immunodeficiency virus (HIV-1) is able to deliver biologically active proteins in vivo. Similarly, the third alpha-helix of Antennapedia homeodomain, and VP22 protein from herpes simplex virus promote the delivery of covalently linked peptides or proteins into cells (reviewed in Ford et al., 2001). Protein delivery based on a short amphipathic peptide carrier, Pep-1, is efficient for delivery of a variety of peptides and proteins into several cell lines in a fully biologically active form, without the need for prior chemical covalent coupling (Morris et al., 2001). The capacity of VP22 chimeric proteins to spread from the primary transduced cell to surrounding cells can improve gene therapy approaches (Zender et al., 2002).

Protein can also be delivered via liposomes. Liposomes have been used as vehicles for drug delivery and gene therapy and they have been shown to have substantial potential in the targeting of specific cell types of the liver. Thus, the use of liposomes may improve targeting efficacy in the treatment of a variety of liver diseases (Wu and Zerm, 1999).

Definitions

"Nucleotide sequence," as used herein, refers to a polymeric form of nucleotides of any length, either ribonucleotides or deoxyribonucleotides. This term refers only to the primary structure of the molecule. Thus, this term includes double- and single-stranded DNA, and RNA. It also includes known types of modifications, for example, methylation, "caps" substitution of one or more of the naturally occurring nucleotides with an analog.

"Overexpression," as used herein, means that the transformed cells do produce more of the overexpressed protein that the untransformed control, when kept under the same condition. Preferably, overexpression is obtained by placing the coding sequence downstream a constitutive promoter.

"Coding sequence" is a nucleotide sequence, which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, recombinant nucleotide sequences or genomic DNA, while introns may be present as well under certain circumstances.

"Protein A20" ("A20") means the TNF-induced zinc finger protein, described by Dixit et al., 1990; Opipari et al., 1990 and Tewari et al., 1995, or an active fragment thereof, such as the zinc finger containing part (amino acids 387–790 of human A20, amino acids 369–775 of murine A20).

The terms "protein" and "polypeptide," as used herein, are interchangeable. Polypeptide refers to a polymer of amino acids and does not refer to a specific length of the molecule. This term also includes post-translational modifications of the polypeptide, such as glycosylation, phosphorylation and acetylation.

"IκB super-repressor" (IκB$^S$) means a non-degradable mutant form of IκB-α, with S32A and S36A mutations, that locks NF-κB in a cytosolic protein complex, preventing its nuclear action.

The invention is further explained by the following illustrative Examples.

EXAMPLES

Example 1

Eneration of the ABIN Adenovirus

The murine ABIN cDNA, N-terminally fused to an E-tag, was amplified via PCR with forward (5'cgggatccgccatgggtgcgccggtgcc3' (SEQ ID NO:6)) and reverse (5'ccccaagcttaaatgacccactgcagcc3' (SEQ ID NO:7)) primers that contained restriction sites for BamHI and HindIII, respectively. The resulting fragment was cloned into a BamHI and HindIII opened pLpA.CMV shuttle vector (Gomez-Foix et al., 1992), and cotransfected with pJM17 (McGrory et al., 1988) by DNA/calcium phosphate coprecipitation in 911 retina cells. In vivo recombination of the shuttle vector expressing the ABIN trangene with the pJM17 backbone resulted in the production of a replication-deficient E1-deleted adenovirus type 5 (AdABIN). A control virus (AdRR5), which does not express a transgene, was generated in a similar way. Following recombination, recombinant plaques were isolated, extracted DNA was verified via PCR, and expression of the correct transgene was confirmed by means of Western Blotting. High titer virusstocks were prepared in HEK293 cells and purified via single CsCl banding. The infectious unit titer was determined in a plaque assay that was performed on confluent HEK293 cells with different virus dilutions. The plaques of lysed cells were counted and calculated as plaque forming units (pfu) per ml virus stock.

Example 2

Expression of ABIN in Vitro Upon Infection with AdABIN

AdABIN was tested for the expression of the transgene in the BWTG3 hepatoma cell line (Szpirer and Szpirer, 1975). Infection with AdABIN was performed at a multiplicity of infection (moi) 100:1. Cells were incubated with virus in a minimal volume of serum-free medium for two hours, after which serum containing medium was added for overnight incubation. For controlling the expression of ABIN, cells were lysed 24 hours after infection and analyzed by SDS-PAGE and immunoblotting with HRP-coupled anti E-tag antibodies (Amersham). Infection with AdABIN resulted in clear expression of ABIN (data not shown).

Efficiency of infection and the subcellular expression pattern of ABIN was analysed by immunofluorescence. In this case, cells were splitted and seeded onto cover slips 24 hours after infection. Another 24 hours later, cells were washed, fixed with 100% methanol at −20° C. for ten minutes and permeabilized with 1% Triton X-100 for ten minutes at room temperature. After blocking with 0.5% BSA for 30 minutes, cells were incubated with 1/3000 dilution of monoclonal anti-E-tag antibody (Amersham) for 90 minutes and with 1/600 dilution of Alexa Fluor 488 goat anti-mouse IgG (Molecular Probes, Eugene, Oreg., US) antibody for 90 minutes. After DAPI nuclear staining, coverslips were mounted with VECTASHIELD™ (Vector Laboratories), and analysed with a Leica DM-IL microscope. This revealed that the efficiency of infection was more than 90%, and that ABIN was exclusively localized in the cytoplasm (data not shown).

Example 3

Inhibition of TNF-Induced NF-κB-Dependent Gene Expression In Vitro by AdABIN

To analyze the effect of ABIN on NF-κB-dependent gene expression, cells were transfected with pNFconluc 24 hours after infection. The latter carries a luciferase reporter gene that is preceded by a minimal promoter and three NF-κB-binding sites (Kimura et al., 1986). Transfection was performed using the FuGene transfection reagent according to the instructions of the manufacturer (Roche Biochemicals). A 6:1 FuGene:DNA ratio was used, and FuGene:DNA mixtures were preincubated for 45 minutes prior to addition to the cells for 24 hours in fresh complete medium. Cells were seeded on 24-well plates and incubated for 24 hours. Then cells were either left untreated or stimulated with 1000 IU/ml TNF. Six hours later, all cells were lysed in 100 μl lysis buffer (25 mM Tris-phosphate pH 7.8, 2 mM DTT, 2 mM CDTA, 10% glycerol and 1% Triton X-100). Luc and Gal activities were analyzed as described previously (De Valck et al., 1996). Luc values were normalized for Gal values in order to correct for differences in transfection efficiency (plotted as luc/gal). AdABIN infection prevented NF-κB-dependent luciferase expression in response to TNF, whereas AdRR5 infection had no effect.

The observation that IκB levels were not changed upon ABIN expression suggests that ABIN does not affect the nuclear translocation of the NF-κB dimer. To analyze the effect of ABIN on the presence of nuclear NF-κB and the binding to a NF-κB-specific DNA probe, cells were left untreated or treated for 30 minutes with 1000 IU/ml mTNF 24 hours after infection. Cells were washed twice with PBS, scraped from the plate and centrifuged for 30 seconds at 12000×g to collect the cells.

Example 4

ABIN does not Significantly Inhibit TNF-Mediated Cell Death

Figure 2:
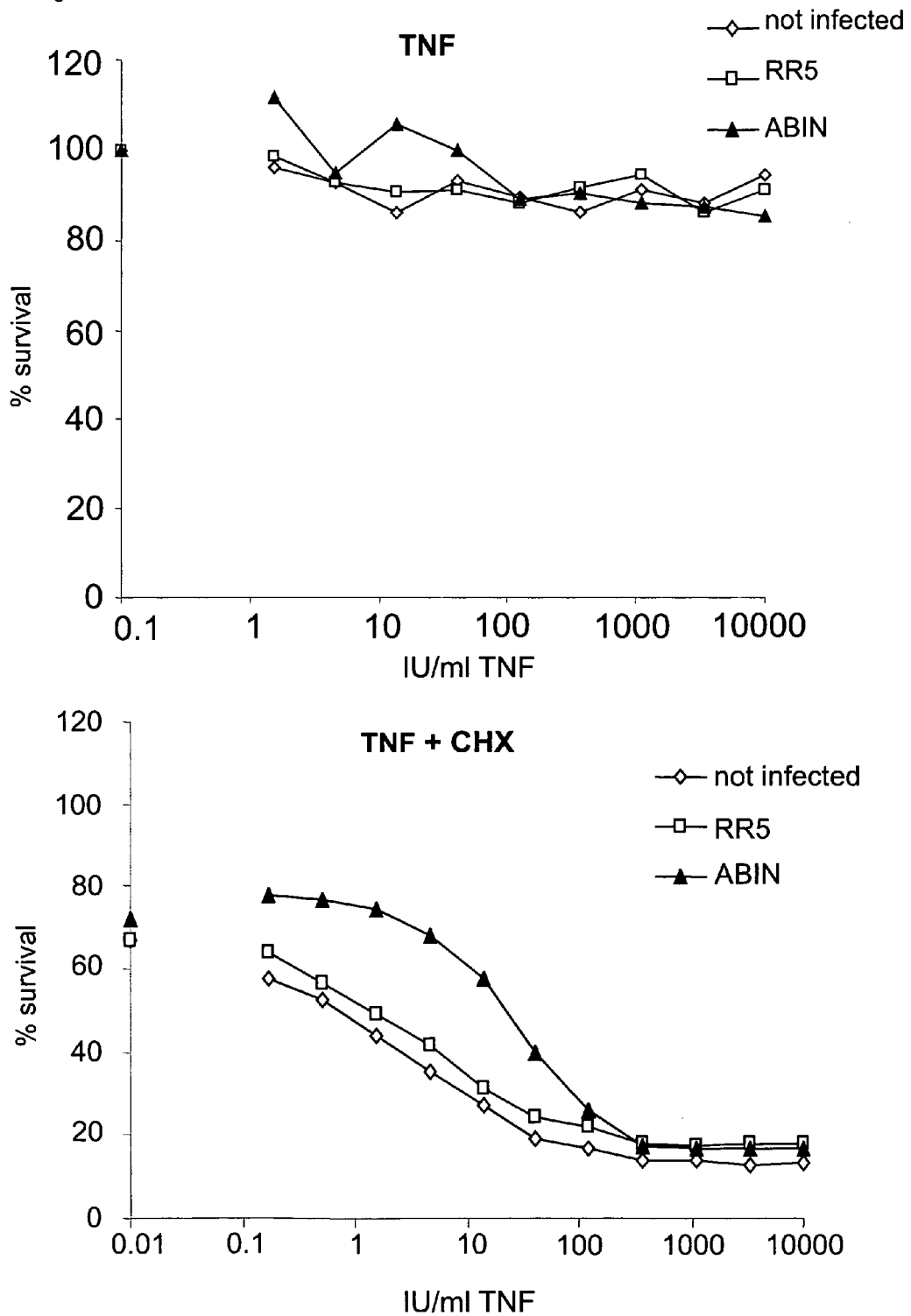
FIG. 2: Effect of AdABIN on TNF-mediated cell death in vitro. AdABIN, AdRR5 or mock-infected BWTG3 cells were seeded in 96-well plates and stimulated with a serial dilution of mTNF in the absence (upper) or presence of CHX (lower) for eight hours. Cell death was analysed upon incubation with MTT.

To investigate if ABIN had an effect on TNF-mediated cell death, AdABIN, AdRR5 or mock-infected BWTG3 cells were incubated with TNF, or combinations of TNF and cycloheximide (CHX). More specifically, 24 hours after infection, cells were seeded in 96-well plates at a density of $4 \times 10^4$ cells per well. Another 24 hours later, cells were stimulated with dilutions of mTNF alone, or with a combination of dilutions of TNF and a constant concentration (10 μg/ml) CHX. Cell death was observed microscopically, and quantitated by incubating the cells with 3-(4,5-dimethylthiazol-2-yl)-2,5-diphenyltetrazolium bromide (MTT) (Tada et al., 1986). After dissolution of the formed crystals, absorbance was determined in an immunoreader (Biorad) at wavelength 595 nm, with 655 nm as reference wavelength. TNF alone had no cytotoxic effect on BWTG3 cells, while TNF+CHX treatment caused cell death by apoptosis. Infection with AdABIN only provided a limited protection against low doses of TNF, while there was no protection at all at higher doses of TNF (FIG. 2).

Example 5

Expression of ABIN in the Liver of AdABIN-Infected Mice

AdABIN was tested for the expression of the transgene and its biological activity in vivo by injecting C57BL/6 mice with $2.5 \times 10^9$ pfu AdABIN into the tail vein. One to six days after infection, mice were sacrificed and livers were isolated. One third of the liver was cut in small pieces and homogenized by douncing in lysis buffer (1% NP-40, 200 mM NaCl, 10 mM Tris-Cl pH 7.5, 5 mM EDTA, 10% glycerol) supplemented with 0.1 mM aprotinine, 1 mM PMSF, and 1 mM gluthation. After 20 minutes incubation on ice, homogenates were centrifuged for 30 minutes at maximal speed in a tabletop centrifuge at 4° C. Protein concentrations were determined by Bradford analysis (Biorad). 50 μg protein was subjected to SDS-PAGE and immunoblotted with HRP-coupled anti E-tag antibody (Amersham). Signals were revealed by ECL (Amersham). ABIN expression was maximal three days after infection and remained high for at least six days (data not shown).

Example 6

Inhibition of TNF/GALN-Induced NF-κB Activation In Vivo by AdABIN and by AD-IκB$^S$ To analyze the effect of AdABIN on TNF/GalN-induced NF-κB activation in the liver, we tested the effect of AdABIN infection on TNF/GalN-induced IκBα degradation by Western blotting. In parallel, the same samples were also analyzed in a gelshift assay for the presence of active NF-κB in nuclear cell extracts of liver. Mice were injected (i.v.) with $2.5 \times 10^9$ pfu Ad-ABIN, Ad-IκB$^s$ (=IκB super-repressor), or AdRR5 (=empty virus control), and challenged after three days by injection with a lethal dosage of TNF (0.3 μg)/GalN (20 mg) diluted in PBS. PBS as such served as a control. Different times after TNF/GalN treatment, mice were killed and liver homogenates were prepared. IκBα expression was analyzed by SDS-PAGE and immunoblotting with polyclonal anti-IκBα antibody (Santa Cruz) (FIG. 1, upper panel). IκBα was almost complete degraded after 0.5 hour TNF/GalN treatment, and reappeared after 1.5 hours. This reappearance is most likely due to de novo synthesis of IκBα in response to TNF. Strong IκBα signals were visible in the AdIκBs-infected mice, in which the expression of the transgene masked the expression of the endogenous gene. Most importantly, in the case of AdABIN-infected animals, IκBα degradation was strongly delayed compared to AdRR5 control mice. These results demonstrate that ABIN inhibits NF-κB activation in the liver of AdABIN-infected mice. NF-κB activation was further analyzed in a gel shift assay of nuclear cell extracts of murine liver. Pieces of murine liver were homogenized by Douncing in 1 ml of swelling buffer (10 mM Hepes pH 7.5, 10 mM KCl, 1 mM MgCl2, 5% glycerol, 0.5 mM EDTA pH7.5, 0.1 mM EGTA pH 7.5, 2 mM Pefablock, 0.5 mM DTT, 0.15 IU/ml aprotinin). After 15 minutes incubation on ice, 65 μl of a 10% NP-40 solution was added, followed by centrifugation at maximum speed in an eppendorff centrifuge for 15 minutes. The pellet was resuspended in 100 μl of nuclear extraction buffer (20 mM Hepes pH 7.5, 1% NP-40, 1 mM MgCl2, 400 mM NaCl, 10 mM KCL, 20% glycerol, 0.5 mM EDTA pH7.5, 0.1 mM EGTA pH 7.5, 2 mM Pefabloc, 0.5 mM DTT, 0.15 IU/ml aprotinin). After centrifugation for 15 minutes at maximum speed in an eppendorff centrifuge, supernatants were stored at −70° C. until use. 10 μl of nuclear lysate was incubated at room temperature for 30 minutes with a $^{32}$P-labeled NF-κB-specific DNA probe (agctagagggasctttccgagagg (SEQ ID NO:8)) in the following buffer: 4% Ficoll 400, 20 mM Hepes pH 7.5, 60 mM KCl, 2 mM DTT, 100 μg/ml poly d(I-C), 1 mg/ml acetylated BSA. Extracts were then run on a 4% native polyacrylamide gel. Radioactivity was visualized by exposure to x-ray films. This showed that AdABIN as well as AdIκBs strongly prevented TNF/GalN-induced nuclear translocation and DNA binding of NF-κB (FIG. 1, lower panel). From this, we can conclude that adenoviral infection with AdABIN or AdIκBα inhibits NF-κB TNF/GalN-induced NF-κB activation in mouse liver.

Example 7

Inhibition of TNF/GALN-Induced Lethal Hepatitis by ABIN

Figure 3:
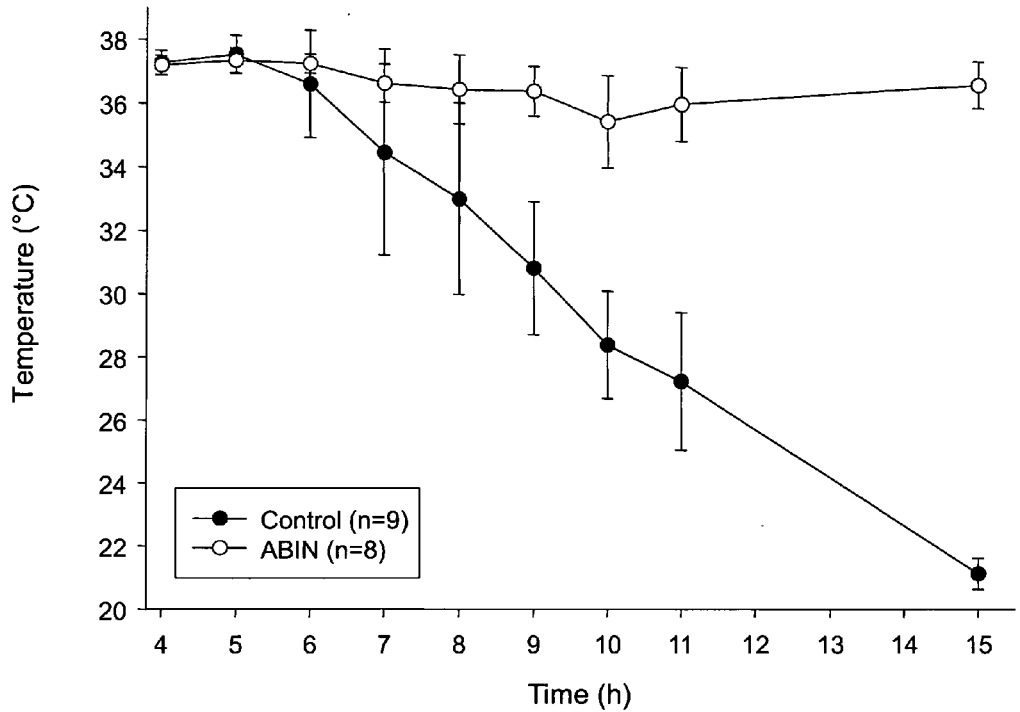
FIG. 3: Effect of AdABIN on TNF/GalN induced body temperature drop in mice. Mice were injected (i.v.) with $2.5 \times 10^9$ pfu AdABIN (n=8) or AdRR5 (=control) (n=9) and challenged three days afterwards with 0.3 μg TNF+20 mg GalN. Temperature (° C.) was measured every hour up to 18 hours after the challenge.
Figure 4:
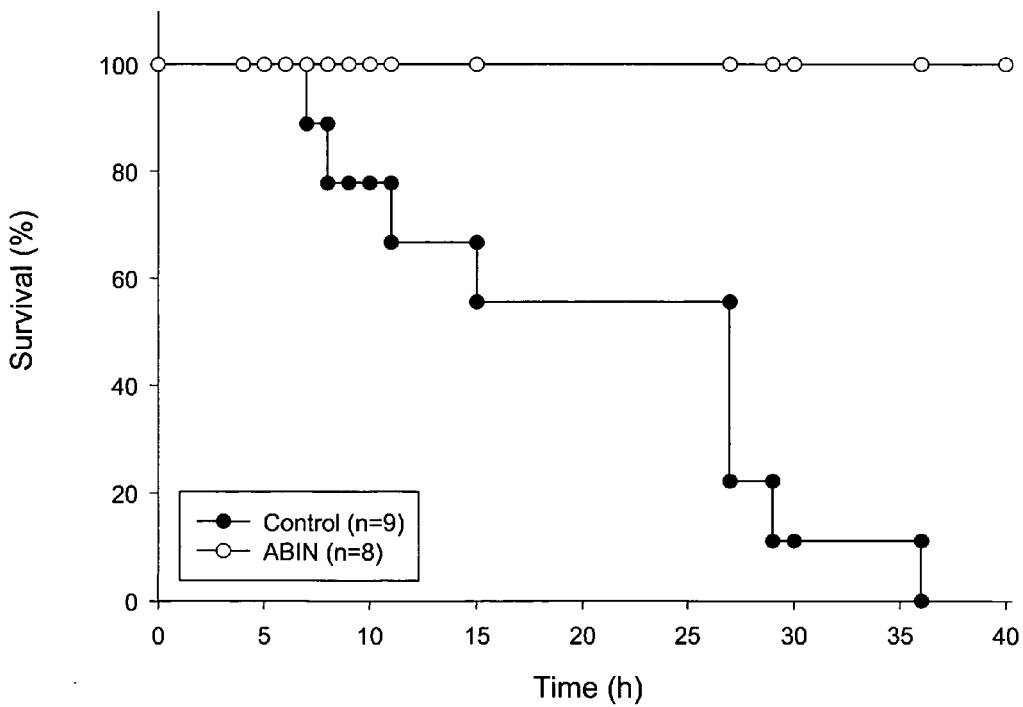
FIG. 4: Effect of AdABIN on TNF/GalN-induced lethality. Mice were injected (i.v.) with $2.5 \times 10^9$ pfu AdABIN (n=8) or AdRR5 (=control) (n=9) and challenged three days afterwards with 0.3 μg TNF+20 mg GalN. Lethality was measured over a period of 72 hours (no further deaths occurred).

To analyze the effect of ABIN on TNF/GalN-induced lethality, C57BL/6 mice were intravenously (i.v.) injected with $2.5 \times 10^9$ pfu of AdABIN (n=8) or AdRR5 (n=9). Three days later, all mice received a lethal dose of TNF/GalN. Every hour, body temperature was measured and lethality was assessed. Control mice showed a drastic fall in body temperature as soon as six hours after injection (FIG. 3), whereas ABIN expressing mice showed a normal body temperature throughout the whole experiment (analyzed up to 18 days after injection). Most importantly, whereas all control mice died over a period of 36 hours, ABIN expressing mice all survived and did now show any signs of illness (FIG. 4).

Figure 5:
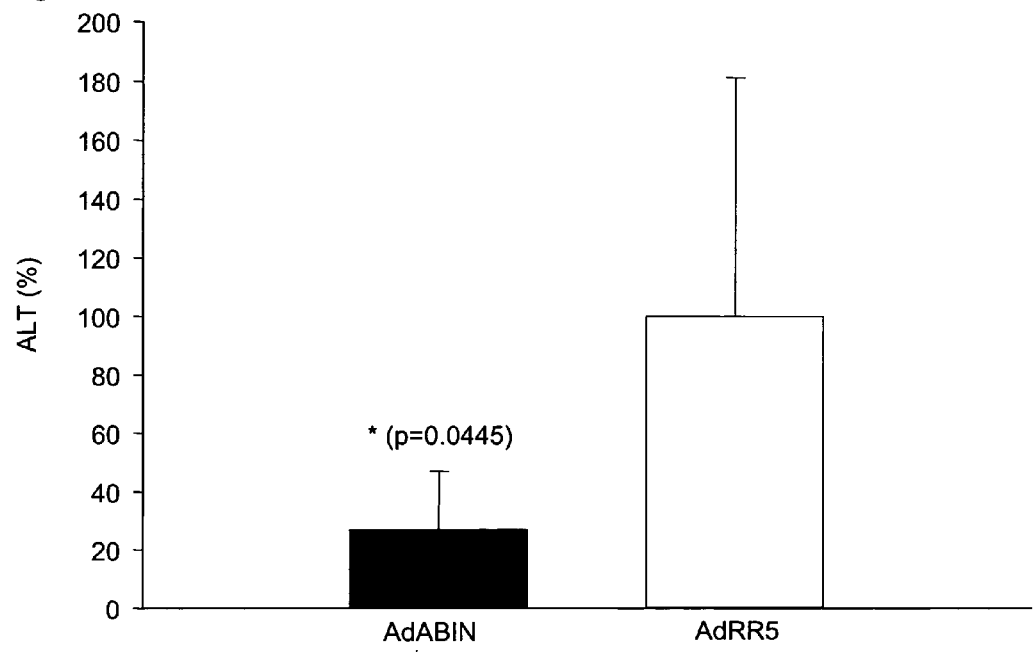
FIG. 5: Effect of AdABIN on TNF/GalN induced alanine amino-transferase (ALT) release in serum. AdABIN or AdRR5-infected mice, challenged with a lethal dose of TNF/GalN were bled eight hours after the injection. Serum was prepared and serum ALT values were measured (in U/L).
Figure 6:
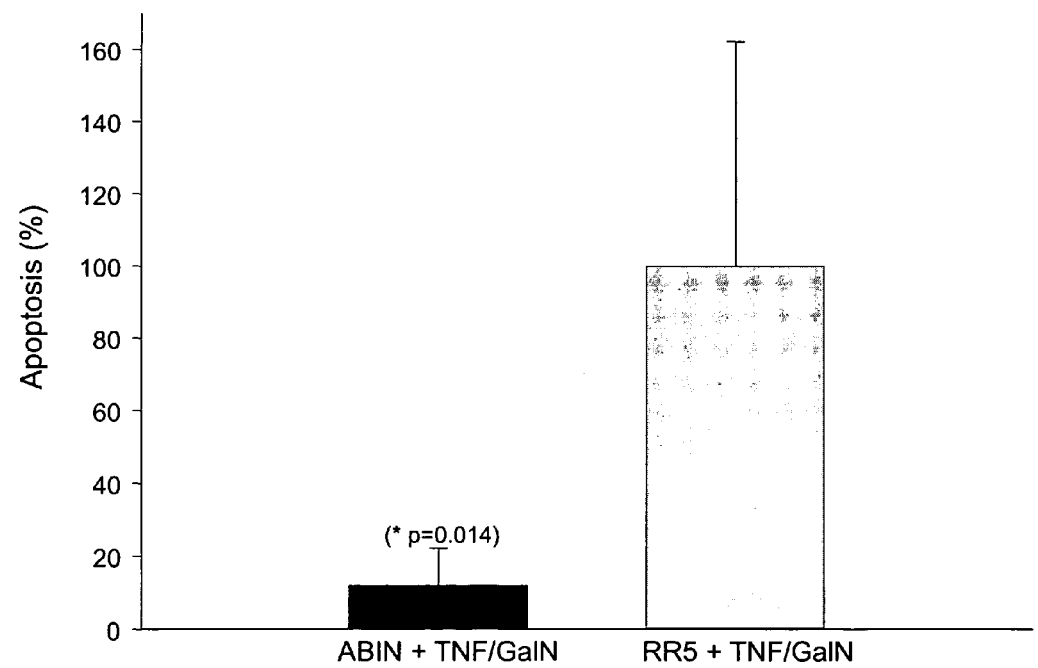
FIG. 6: Effect of AdABIN on TNF/GalN induced DNA fragmentation in the liver. Livers of AdABIN or AdRR5-infected mice were isolated eight hours after a challenge with a lethal dose of TNF/GalN. DNA fragmentation was measured by ELISA, and is expressed as a percentage of control mice (AdRR5).
Figure 7:
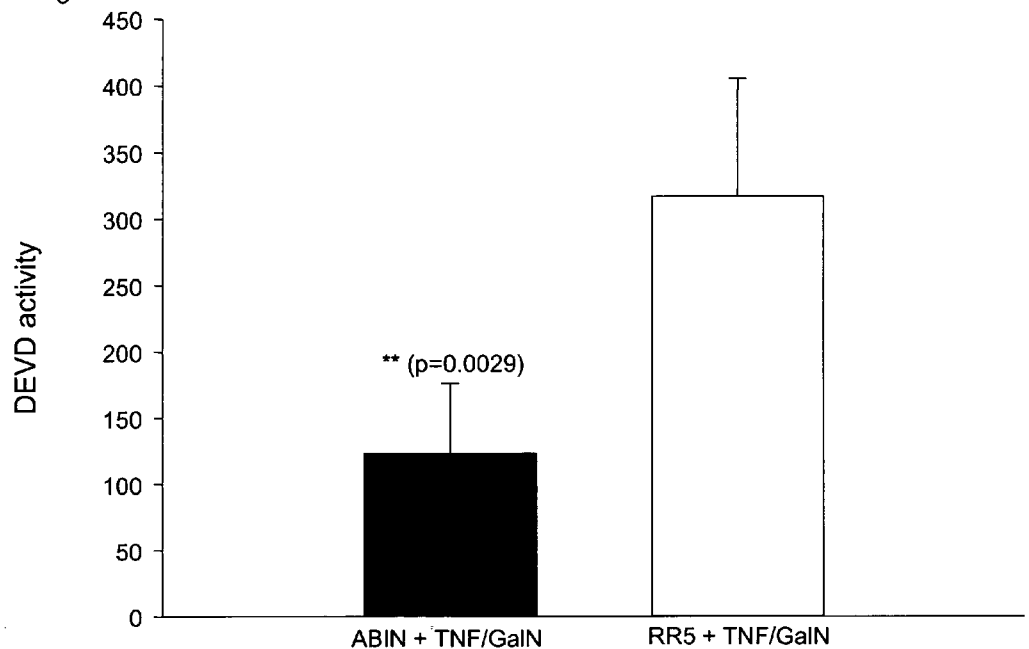
FIG. 7: Effect of AdABIN on TNF/GalN induced caspase activity in liver homogenates. AdABIN or AdRR5-infected mice (n=5 each) were treated with TNF+GalN for eight hours. 30 μg of liver homogenate was tested for its proteolytic activity on Ac-DEVD.AMC. Proteolytic activity is expressed as the increase in AMC fluorescence as a function of time (ΔF/min).
Figure 8:
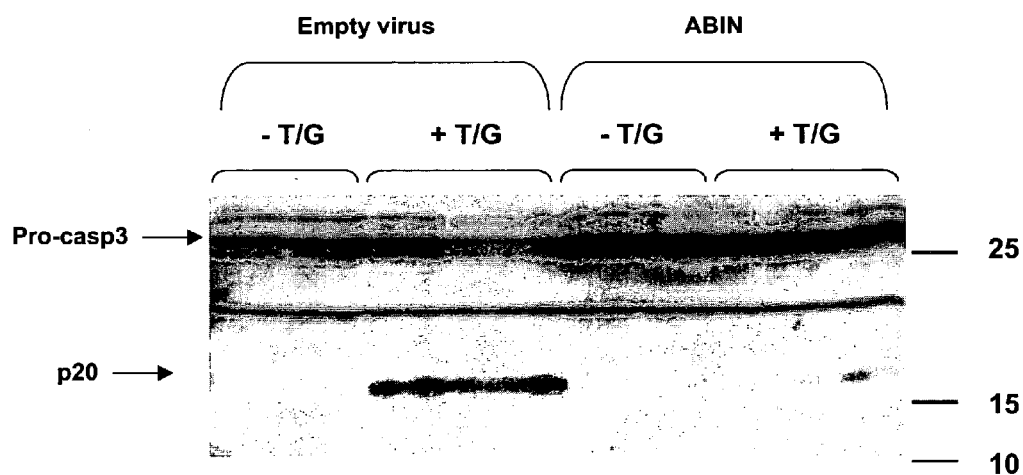
FIG. 8: Effect of AdABIN on TNF/GalN induced cleavage of caspase-3 in liver homogenates. AdABIN or AdRR5-infected mice were left untreated (n=4) or injected (n=5) with TNF+GalN for eight hours. Liver homogenates were prepared; proteins were separated by 15% SDS-PAGE, and immunoblotted using a polyclonal anti-caspase-3 antibody. Inactive pro-caspase-3 as well as the p20 subunit of caspase-3 that is proteolytically released are indicated by an arrow.

To analyze the effect of ABIN on liver toxicity, mice were injected with AdABIN (n=5) or AdRR5 (n=5) as described above, followed after three days by injection with a lethal dosis of TNF/GalN. At the time that AdRR5 mice showed a strong decrease in body temperature, animals were sacrificed for histology and biochemistry studies. Blood was collected from AdRR5 and AdABIN mice, and livers were prepared for further analysis. The concentration of alanine aminotransferase (ALT) in the blood after TNF/GalN injection was determined using an enzymatic/colorimetric kit (Sigma Chemical Company), and served as a parameter for liver necrosis (Reutter et al., 1968). Blood was taken from the retro-orbital plexus under light ether anesthesia and was allowed to clot for 30 minutes at 37° C. and one hour at 4° C., followed by centrifugation at 16,000×g. Serum was stored at −20° C. ALT levels were significantly diminished in AdABIN-infected mice when compared to control mice (FIG. 5). DNA fragmentation and caspase activation were analyzed as parameters for apoptosis. DNA fragmentation was measured by immunochemical determination of histon-complexed DNA fragments in a microtiter plate (Salgame et al. 1997). Briefly, plates were coated with an Ab directed against histon H2B. After blocking, liver homogenates were added and a biotinylated detection Ab specific for the nucleosome subparticle of histones H2A, H$_2$B, and DNA was administered. Detection was performed with alkaline phosphatase-conjugated streptavidin (Sanvertech, Boechout, Belgium) and substrate (Sigma). Signals obtained with samples from TNF/GalN-treated mice were set as 100%. These experiments show that TNF/GalN-induced DNA fragmentation is significantly reduced in AdABIN-infected animals (FIG. 6). Caspase activation was revealed by the hydrolysis of Ac-DEVD-amc upon incubation with liver cell extracts. Briefly, 30 μg of liver homogenate was incubated in 200 ul cell free system buffer (10 mM Hepes pH 7.5, 220 mM Mannitol, 68 mM Sucrose, 2 mM NaCl, 2 mM MgCl$_2$, 2.5 mM KH$_2$PO$_4$, 10 mM DTT) in the presence of 50 μM Ac-DEVD.amc (Peptide Institute; Osaka, Japan), for 60 minutes at 30° C. Release of 7-amino-4-methyl coumarin (AMC) was monitored during 60 minutes in a fluorometer (CytoFluor; PerSeptive Biosystems; Cambridge, Mass., USA) at an excitation wavelength of 360 nm and an emission wavelength of 409 nm. Data are expressed as increase in fluorescence as a function of time (AF/min). Hydrolysis of Ac-DEVD-AMC upon incubation with liver homogenates of TNF/GalN treated mice was significantly reduced in AdABIN-infected animals (FIG. 7). Similarly, inhibition of TNF/GalN-induced caspase activation upon AdABIN infection was also demonstrated by inhibition of the proteolytic maturation of caspase-3, as revealed by SDS-PAGE and immunoblotting with caspase-3-specific polyclonal antibodies (FIG. 8).

As shown by histology, TNF/GalN-induced lethal hepatitis is associated with total tissue destruction of the parenchymal tissue, influx of erythrocytes (hemorrhage) at the site of the sinusoids and apoptosis and necrosis of the hepatocytes. In addition, a massive influx of macrophages and neutrophils in the liver can be observed. Livers of AdABIN pretreated mice show better preservation of the tissue integrity and nearly no hemorrhage. In contrast to the complete protection against TNF/GalN-induced lethality, hepatocyte cell death, and hemorrhage, infiltration of white blood cells was only partially reduced by in vivo expression of ABIN.

Figure 9:
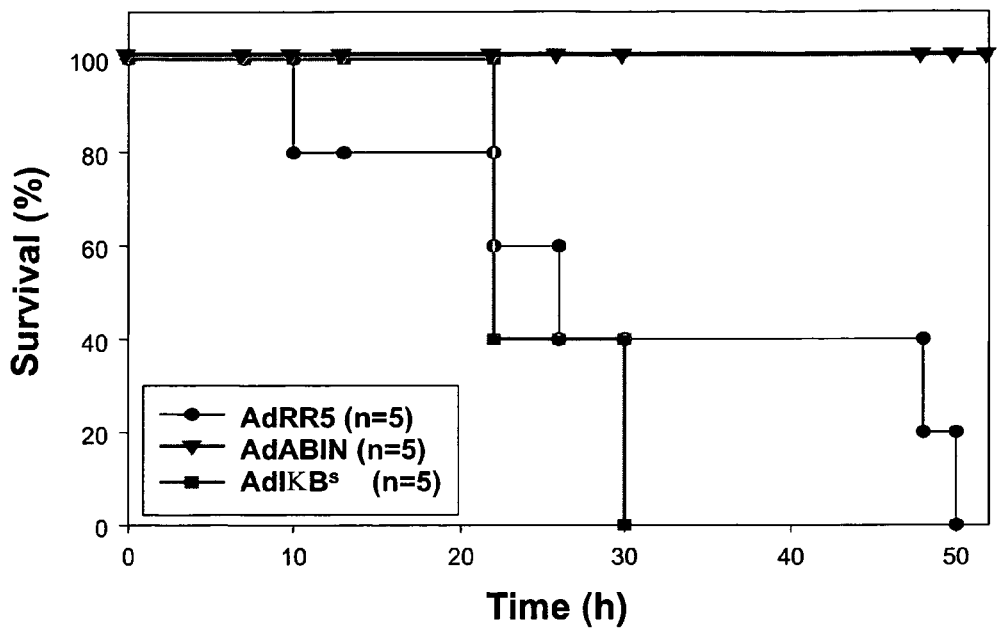
FIG. 9: Comparison of AdABIN and AdIκBs on TNF/GalN-induced lethality. Mice were injected (i.v.) with $2.5 \times 10^9$ pfu AdABIN (n=5), AdIκBs (n=5) or AdRR5 (=control) (n=9) and challenged three days afterwards with 0.3 μg TNF+20 mg GalN. Lethality was measured over a period of seven days.

As mentioned earlier, blanket inhibition of hepatic NF-κB activation may lead to both beneficial and detrimental effects. Indeed, adenoviral administration of a dominant IκBA superrepressor does not protect against TNF/GalN-induced lethality. In the same experiment, adenoviral administration of ABIN completely protected the mice (FIG. 9). At this moment, a clear explanation for the different effect of ABIN and IκB$^S$ cannot be given. However, it should be mentioned that ABIN, in contrast to IκBα, inhibits NF-κB activation upstream of the IKK complex. Because stimulus-specific differences in NF-κB signalling have been shown upstream of the IKK complex, it is not unlikely that ABIN-mediated inhibition of NF-κB-dependent gene expression is limited to a selection of NF-κB responsive genes. Such a possible slective inhibition of NF-κB-dependent genes might shift a balance between sensitizing and protective proteins, which could result in a net protective effect of this inhibitor. Alternatively, we cannot exclude NF-κB independent effects of ABIN in the protection against TNF-induced liver failure.

Figure 10:
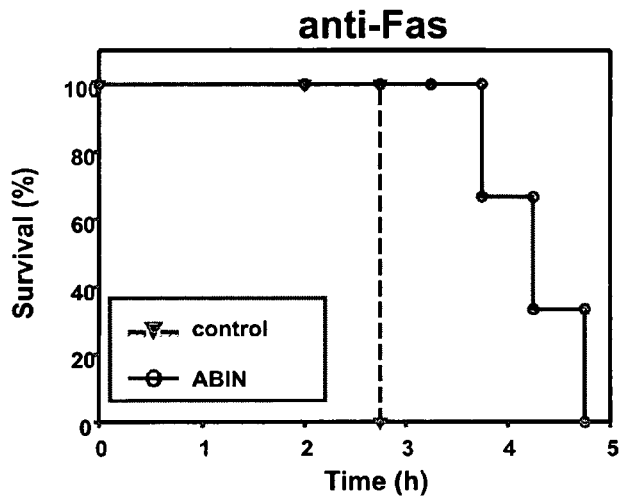
FIG. 10: Effect of AdABIN on anti-Fas-induced lethality. Mice were injected (i.v.) with $2.5 \times 10^9$ pfu AdABIN (n=3) or AdRR5 (=control) (n=3) and challenged three days afterwards with 10 μg anti-Fas. Lethality was measured over a period of five hours.
Figure 11:
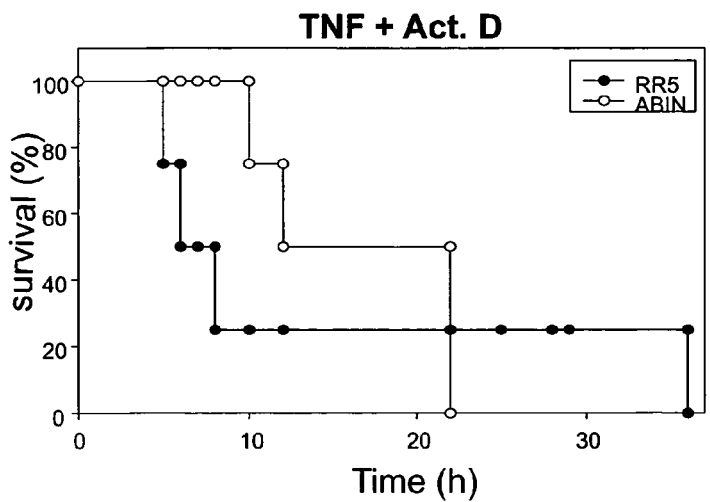
FIG. 11: Effect of AdABIN on TNF/ActD-induced lethality. Mice were injected (i.v.) with $2.5 \times 10^9$ pfu AdABIN (n=5) or AdRR5 (=control) (n=5) and challenged three days afterwards with 0.3 μg TNF+20 μg ActD (actinomycin D). Lethality was measured over a period of 35 hours.

Fas is an apoptosis-signalling cell surface molecule that triggers cell death upon specific ligand or antibody binding. Treatment of mice with an anti-Fas antibody causes fulminant hepatic failure due to massive apoptosis (Ogasawara et al., 1993). In contrast to TNF/GalN, anti-Fas does not lead to NF-κB activation and an inflammatory response in the liver, but rather induces a direct apoptotic response. To examine the susceptibility of AdABIN-infected mice to anti-Fas-mediated lethality, mice were injected with AdRR5 or AdABIN as described above, and three days later (i.v.) injected with 10 μg anti-Fas (Pharmingen). Both AdRR5 and AdABIN pretreated mice died within three to five hours following administration of anti-Fas (FIG. 10). This demonstrates that ABIN does not significantly influence the signalling pathway of Fas-mediated apoptosis. To further investigate whether the difference in protection in the TNF/GalN versus the anti-Fas-induced liver failure is due to a difference in receptor involvement (TNF-receptor versus Fas) or reflects a difference in the role of apoptosis and gene-dependent effects, we also analyzed the effect of AdABIN on TNF-induced lethality in actinomycin D sensitized mice. Actinomycin D blocks cellular transcription, and sensitizes cells to the direct apoptotic effect of TNF, without a contribution of an inflammatory component. Therefore, mice were injected with AdRR5 or AdABIN as described above, and three days later (i.v.) injected with 0.3 μg TNF and 20 μg actinomycin D. Both AdRR5 and AdABIN pretreated mice died within 20 to 35 hours following administration of TNF/ActD (FIG. 11). Taken together, these results suggest that ABIN-mediated protection against TNF/GalN-induced liver failure involves a transcription-dependent event.

REFERENCES

Altschul, S. F., Madden, T. L., Schäffer, A. A., Zhang, J., Zhang, Z., Miller, W. And Lipman, D. J. (1997) *Nucleic Acids Res* 25, 3389–3402.

Arvelo, M. B., Cooper, J. T., Longo, C., Daniel, S., Grey, S. T., Mahiou, J., Czismadia, E., Abu-Jawdeh, G., and Ferran, C., (2002) *Hepatology* 35, 535–543.

Beg, A. A., Sha, W. C., Bronson, R. T., Ghosh, S., and Baltimore, D. (1995) *Nature* 376, 167–170.

Behr, J. P. (1994) *Bioconjugate Chem.* 5, 382–389.

Bellas, R. E., FitzGerald, M. J., Fausto, N., and Sonenshein, G. E. (1997) *American Journal of Pathology* 151, 891–896.

Beyaert, R., Heyninck, K., and Van Huffel, S. (2000) *Biochem Pharmacol* 60(8), 1143–1151.

Bird, G., Sheron, N., Goka, A., Alexander, G., and Williams, R. (1990) *Ann Intern Med* 112, 917–20.

Blaese, R. M., Culver, K. M., Miller, A. D., Carter, C. S., Fleisher, T., Clerici, M., Shearer, G., Chang, L., Tolstoshev, P., et al. (1995) *Cancer Gene Ther.* 2, 291–197.

Chen, Q., and Cederbaum, A. (1997) *Molecular Pharmacology* 52, 648–657.

Crystal, (1995) *Science* 270, 404–410.

Decker, K., and Keppler, D. (1974) *Rev. Physiol. Biochem. Pharmacol.* 71, 77–106.

De Valck, D., Heyninck, K., Van Criekinge, W., Contreras, R., Beyaert, R., and Fiers, W. (1996) *Febs Letters* 384(1), 61–64.

Diehl, A., Yin, M., Fleckenstein, J., Yang, S., Lin, H., Brenner, D. A., Westwick, J., Bagby, G., and S, N. (1994) *Am J Physiol* 267 (Gastrointest. Liver Physiol. 30), G552–G561.

Dixit V. M., Green, S., Sarma, V., Holzman, L. B., Wolf, F. W., O'Rourke, K., Ward, P. A., Prochownik, E. V. and Marks, R. M. (1990) *J Biol Chem* 265, 2973–2978.

Freshney et al., *Culture of Animal Cells, A Manual of Basic Technique* ($3^{rd}$ ed. 1994)

Ford, K. G., Souberbielle, B. E., darling, D., and Farzanch, F. (2001) *Gene Ther.* 8, 1–4.

Gao, X. and Huang, L. (1995) *Gene Therapy* 2, 710–722

Gomez-Foix, A., Coats, W., Baque, S., Alam, T., Gerard, R., and Newgard, C. (1992) *Journal of Biological Chemistry* 267, 25129.

Gonzalez-Amaro, R., Garcia-Monzon, C., Garcia-Buey, L., Moreno-Otero, R., Alonso, J., Yague, E., Pivel, J., Lopez-Cabrera, M., Femandez-Ruiz, E., and Sanchez-Madrid, F. (1994) *Journal of Experimental Medicine* 179, 841–848.

Grove, J., Daly, A. K., Bassendine, M. F., and Day, C. (1997) *Hepatology* 26, 143–146.

Gupta, K., Ott, D., Hope, T. J., Siliciano, R. F. and Boecke, J. D. (2000) *J Virol* 74, 11811–11824.

Hermonat, and Muzyczka, (1984) *Proc. Natl. Acad. Sci. USA* 81, 6466–6470.

Heyninck, K., De Valck, D., Vanden Berghe, W., Van Criekinge, W., Contreras, R., Fiers, W., Haegeman, G., and Beyaert, R. (1999) *J Cell Biol* 145(7), 1471–1482.

Iimuro, Y., Nishiura, T., Hellerbrand, C., Behrns, K. E., Schoonoven, R., Grisham, J. W., and Brenner, D. A. (1998) *Journal of Clinical Investigation* 101, 802–811.

Kimura, A., Israel, A., Le Bail, O., and Kourilsky, P. (1986) *Cell* 44, 261.

Kotin, R. M. (1994) *Human Gene Therapy* 5, 793–801.

Larrea, E., Garcia, N., Qian, C., Civeira, M., and Prieto, J. (1996) *Hepatology* 23, 210–217.

Lee, E. G., Boone, D. L., Chai, S., Libby, S. L., Chien, M., Lodolce, J. P., and Ma, A. (2000) *Science* 289, 2350–2354.

Leist, M., Gantner, F., Jilg, S., and Wendel, A. (1995) *Journal of Immunology* 154, 1307–1316.

Majumder, M., Ghosh, A. K., Steele, R., Zhou, X. Y., Philips, N. J., Ray, R., and Ray, R. B. (2002) *Virology* 294, 94–105.

McClain, C. (1991) *Hepatology* 14, 394–396.

McGrory, W., Bautista, D., and Graham, F. (1988) *Virology* 163, 614.

Morris, M. C., Depolier, J., Mery, J., Heitz, F., Divita, G. (2001) *Nat. Biotechnol.* 19, 1173–1176.

Muto, Y., Nouri-Aria, K., Meager, A., Alexander, G., Eddleston, A., and Williams, R. (1988) *Lancet* 2, 72–74.

Ogasawara, J., Watanabe-Fukunaga, R., Adachi, M., Matsuzawa, A., Kasugai, T., Kitamura, Y., Itoh, N., Suda, T., and Nagata, S. (1993) *Nature* 364, 806–809.

Opipari, A. W., Boguski, M. S. and Dixit, V. M. (1990) *J Biol Chem* 265, 14705–14708.

Park, K.-J., Cho, S.-H., Lee, S. Y., Hwang, S. B., and Lai, M. M. C. (2002) *J. Biol. Chem.* 277, 13122–13128.

Ray, R. B., Meyer, K., Steele, R., Shrivastava, A., Aggarwal, B. B., and Ray, R. (1998) *Journal of Biological Chemistry* 273, 2256–2259.

Remy, J. S., Seerlin, C., Vierling, P. and Behr, J. P. (1994) *Bioconjugate Chem.* 5, 647–654.

Reutter, W., Lesch, R., Keppler, D., and Decker, K. (1968) *Naturwissenschaften* 55, 497.

Salgame, P., Varadhachary, A. S., Primiano, L. L., Fincke, J. E., Muller, S., and Monestier, M. (1997) *Nucleic Acids Research* 25, 680.

Samulski, R. J., Chang, L. S. and Shenk, T. (1989) *J. Virol.* 63, 3822–3828.

Szpirer, C., and Szpirer, J. (1975) *Differentiation* 4(2), 85–91.

Tada, H., Shiho, O., Kuroshima, K., Koyama, M., and Tsukamoto, K. (1986) *J Immunol Methods* 6, 157–165.

Tewari, M., Wolf, F. W., Seldin, M. F., O'Shea, K. S., Dixit, V. M. and Turka, L. A. (1995) *J Immunol* 154, 1699–1706.

Tiegs, G., Wolter, M., and Wendel, A. (1989) *Biochem Pharmacol* 38, 627–631.

Van Huffel, S., Delaei, F., Heyninck, K., De Valck, D., and Beyaert, R. (2001) *Journal of Biological Chemistry* 276, 30216–30223.

Van Molle, W., Denecker, G., Rodriguez, I., Brouckaert, P., Vandenabeele, P., and Libert, C. (1999) *Journal of Immunology* 163, 5235–5241.

Wu, J, and Zem, M. A. (1999) *Front. Biosci.* 4, D520-D527.

Xu, Y., Bialik, S., Jones, B. E., Iimuro, Y., Kitsis, R., Srinivasan, A., Brenner, D. A., and Czaja, M. (1998) *American Journal of Physiology* 275, C1058-C1066.

Zender, L., Kuhnel, F., Kock, R., Manns, M., Kubicka, S. (2002) *Cancer Gene Ther.* 9, 489–496.

---

What is claimed is:

1. A method of treating tumor necrosis factor-induced (TNF-induced) liver failure in a subject, the method comprising:
   administering to the subject an isolated A20-binding inhibitor of NF-κB activation (ABIN), wherein said ABIN comprises the consensus amino acid sequence depicted in SEQ ID NO:4, SEQ ID NO:5, or combination of SEQ ID NO:4 and SEQ ID NO:5; and wherein said treatment results in a significant reduction of liver apoptosis and liver necrosis in the subject.

2. The method according to claim 1, wherein the TNF-induced liver failure is of viral hepatitis, fulminant hepatitis and/or alcoholic liver disease origin.

* * * * *

SEQUENCE LISTING

```
<160> NUMBER OF SEQ ID NOS: 8

<210> SEQ ID NO 1
<211> LENGTH: 2812
<212> TYPE: DNA
<213> ORGANISM: Mus musculus
<220> FEATURE:
<221> NAME/KEY: CDS
<222> LOCATION: (117)..(2060)
<220> FEATURE:
<221> NAME/KEY: CDS
<222> LOCATION: (276)..(2060)
<220> FEATURE:
<221> NAME/KEY: intron
<222> LOCATION: (81)..(252)

<400> SEQUENCE: 1
cacagggagg catggccgca ctcactgggc acatcttcag atcacctcgt gcattctcgg      60
atgagtgacc tgggctgaag ctaggcggcc gtcacggcag gggttgagcc accctc atg    119
                                                                Met
                                                                  1 gaa ggg aga gga ccc tac cgg atc tac gac cca ggg ggc agc acg cct      167
Glu Gly Arg Gly Pro Tyr Arg Ile Tyr Asp Pro Gly Gly Ser Thr Pro
         5                  10                  15 ctg gga gag gtg tcc gca gct ttt gaa cgt cta gtg gag gag aat act      215
Leu Gly Glu Val Ser Ala Ala Phe Glu Arg Leu Val Glu Glu Asn Thr
     20                  25                  30 cgg ctg aag gga aaa atg caa ggg ata aag atg tta ggg gag ctt ctg      263
Arg Leu Lys Gly Lys Met Gln Gly Ile Lys Met Leu Gly Glu Leu Leu
 35                  40                  45 gag gag tct cag atg gaa gcg tcc aga ctc cgg cag aag gca gag gag      311
Glu Glu Ser Gln Met Glu Ala Ser Arg Leu Arg Gln Lys Ala Glu Glu
 50                  55                  60                  65 ctg gtc aag gac agc gag ctg tca cca ccg aca tct gcc ccc tcc ttg      359
Leu Val Lys Asp Ser Glu Leu Ser Pro Pro Thr Ser Ala Pro Ser Leu
                 70                  75                  80 gtc tcc ttt gat gac ctg gct gag ctc aca gga cag gat aca aag gtc      407
Val Ser Phe Asp Asp Leu Ala Glu Leu Thr Gly Gln Asp Thr Lys Val
```

-continued

|  |  |  |  |  |  | 85 |  |  |  |  | 90 |  |  |  |  | 95 |  |  |
|---|---|---|---|---|---|---|---|---|---|---|---|---|---|---|---|---|---|---|

```
cag gta cat cct gct acc agc act gcc gcc acc acc acc gcc acc gcc       455
Gln Val His Pro Ala Thr Ser Thr Ala Ala Thr Thr Thr Ala Thr Ala
            100                 105                 110 acc acg gga aac tcc atg gag aag ccc gag cca gcc tcc aaa tct ccg       503
Thr Thr Gly Asn Ser Met Glu Lys Pro Glu Pro Ala Ser Lys Ser Pro
        115                 120                 125 tcc aat ggc gcc tcc tcg gac ttt gaa gtg gtc cct act gag gag cag       551
Ser Asn Gly Ala Ser Ser Asp Phe Glu Val Val Pro Thr Glu Glu Gln
130                 135                 140                 145 aat tca ccc gaa act ggc agc cac cct acg aac atg atg gac ctg ggg       599
Asn Ser Pro Glu Thr Gly Ser His Pro Thr Asn Met Met Asp Leu Gly
                150                 155                 160 ccc cca ccc cca gag gac agc aac ctg aag ctc cac ctg cag cgc ctg       647
Pro Pro Pro Pro Glu Asp Ser Asn Leu Lys Leu His Leu Gln Arg Leu
            165                 170                 175 gag acc acc ctt agc gtg tgt gca gag gag cca gac cac agc cag ctc       695
Glu Thr Thr Leu Ser Val Cys Ala Glu Glu Pro Asp His Ser Gln Leu
        180                 185                 190 ttc acc cac ctg ggc cgc atg gcc ctc gag ttc aac agg ttg gcc tcc       743
Phe Thr His Leu Gly Arg Met Ala Leu Glu Phe Asn Arg Leu Ala Ser
    195                 200                 205 aaa gtg cat aaa aat gag cag cgc acc tcc atc ctg cag acc tta tgt       791
Lys Val His Lys Asn Glu Gln Arg Thr Ser Ile Leu Gln Thr Leu Cys
210                 215                 220                 225 gag cag ctg cgc cag gag aat gaa gcc ctg aag gcc aag ctg gac aag       839
Glu Gln Leu Arg Gln Glu Asn Glu Ala Leu Lys Ala Lys Leu Asp Lys
                230                 235                 240 ggc ctg gaa cag cgg gat ctg gct gct gag agg ctg cgg gag gaa aac       887
Gly Leu Glu Gln Arg Asp Leu Ala Ala Glu Arg Leu Arg Glu Glu Asn
            245                 250                 255 acg gag ctc aag aaa ctg ttg atg aac agc agc tgc aaa gag gga ctc       935
Thr Glu Leu Lys Lys Leu Leu Met Asn Ser Ser Cys Lys Glu Gly Leu
        260                 265                 270 tgt ggg cag ccc agc tcc cca aag cca gag ggt gct ggc aag aag ggc       983
Cys Gly Gln Pro Ser Ser Pro Lys Pro Glu Gly Ala Gly Lys Lys Gly
    275                 280                 285 gtg gct gga cag cag cag gcc agt gtg atg gcg agt aaa gtc cct gaa       1031
Val Ala Gly Gln Gln Gln Ala Ser Val Met Ala Ser Lys Val Pro Glu
290                 295                 300                 305 gcg ggg gcc ttt gga gca gct gag aag aaa gtg aag ttg cta gaa cag       1079
Ala Gly Ala Phe Gly Ala Ala Glu Lys Lys Val Lys Leu Leu Glu Gln
                310                 315                 320 caa cgc atg gag ctg ctg gaa gtg aac aag cag tgg gac cag cat ttc       1127
Gln Arg Met Glu Leu Leu Glu Val Asn Lys Gln Trp Asp Gln His Phe
            325                 330                 335 cgg tcc atg aag cag cag tat gag cag aag atc aca gag ctt cgc cag       1175
Arg Ser Met Lys Gln Gln Tyr Glu Gln Lys Ile Thr Glu Leu Arg Gln
        340                 345                 350 aag ctg gtg gac ctg cag aaa cag gta act gag ctg gag gcc gaa cgg       1223
Lys Leu Val Asp Leu Gln Lys Gln Val Thr Glu Leu Glu Ala Glu Arg
    355                 360                 365 gag cag aag cag cgt gac ttt gac cgg aaa ctc ctc ctg gcc aaa tcg       1271
Glu Gln Lys Gln Arg Asp Phe Asp Arg Lys Leu Leu Leu Ala Lys Ser
370                 375                 380                 385 aag ata gag atg gaa gag acc gac aag gag cag ctg aca gca gag gcc       1319
Lys Ile Glu Met Glu Glu Thr Asp Lys Glu Gln Leu Thr Ala Glu Ala
                390                 395                 400 aag gaa ctg cgc cag aag gtc agg tac cta cag gat cag ctg agc ccg       1367
```

-continued

```
                Lys Glu Leu Arg Gln Lys Val Arg Tyr Leu Gln Asp Gln Leu Ser Pro
                                405                 410                 415 ctc aca agg caa cga gaa tac cag gag aag gag atc cag cgg ctc aat            1415
Leu Thr Arg Gln Arg Glu Tyr Gln Glu Lys Glu Ile Gln Arg Leu Asn
            420                 425                 430 aag gcc ctg gag gag gcc ctc agc atc cag gcc tct cca tca tct ccg            1463
Lys Ala Leu Glu Glu Ala Leu Ser Ile Gln Ala Ser Pro Ser Ser Pro
        435                 440                 445 cct gca gct ttt ggg agt cca gaa ggc gtt ggg ggc cat ctg agg aag            1511
Pro Ala Ala Phe Gly Ser Pro Glu Gly Val Gly Gly His Leu Arg Lys
450                 455                 460                 465 cag gaa cta gtg aca cag aat gag ttg ctg aaa cag cag gta aag atc            1559
Gln Glu Leu Val Thr Gln Asn Glu Leu Leu Lys Gln Gln Val Lys Ile
                470                 475                 480 ttt gaa gag gac ttc cag agg gaa cgg agt gac cgt gaa cgc atg aat            1607
Phe Glu Glu Asp Phe Gln Arg Glu Arg Ser Asp Arg Glu Arg Met Asn
            485                 490                 495 gaa gag aag gag gag ctg aag aag caa gta gag aag ctg cag gcc cag            1655
Glu Glu Lys Glu Glu Leu Lys Lys Gln Val Glu Lys Leu Gln Ala Gln
        500                 505                 510 gtc acc ctg act aat gcc cag ctc aaa act ctc aaa gag gag gag aag            1703
Val Thr Leu Thr Asn Ala Gln Leu Lys Thr Leu Lys Glu Glu Glu Lys
    515                 520                 525 gcc aag gaa gcc ctc aaa cag cag aag agg aaa gca aag gct tcg gga            1751
Ala Lys Glu Ala Leu Lys Gln Gln Lys Arg Lys Ala Lys Ala Ser Gly
530                 535                 540                 545 gag cgc tac cac atg gaa ccc cac cct gag cac gtc tgc ggc gcc tat            1799
Glu Arg Tyr His Met Glu Pro His Pro Glu His Val Cys Gly Ala Tyr
                550                 555                 560 ccc tat gcc tac cca ccc atg cca gcc atg gta cct cac cat gcc tac            1847
Pro Tyr Ala Tyr Pro Pro Met Pro Ala Met Val Pro His His Ala Tyr
            565                 570                 575 aag gac tgg tcc cag atc cga tac cct cca ccc cct gtg ccc atg gag            1895
Lys Asp Trp Ser Gln Ile Arg Tyr Pro Pro Pro Pro Val Pro Met Glu
        580                 585                 590 cac ccg ccc cca cac ccc aac tct cgc ctc ttc cat ctg ccg gag tac            1943
His Pro Pro Pro His Pro Asn Ser Arg Leu Phe His Leu Pro Glu Tyr
    595                 600                 605 acc tgg cgt cca ccc tgt gca ggg att cgg aat cag agc tct caa gtg            1991
Thr Trp Arg Pro Pro Cys Ala Gly Ile Arg Asn Gln Ser Ser Gln Val
610                 615                 620                 625 atg gac ccg ccc cca gac agg cct gca gag cca gag tct gca gac aat            2039
Met Asp Pro Pro Pro Asp Arg Pro Ala Glu Pro Glu Ser Ala Asp Asn
                630                 635                 640 gac tgt gat ggg ccc cag tga     ggctgcagtg ggtcatttgg ttccaccttc           2090
Asp Cys Asp Gly Pro Gln
                645 atctttcaga gccagctgac ctcagattgc caaaagtttg aaggccatgt gcatgttctg          2150 tgtgacccaa gccttggcag aggagaggct gggatgggta gctggctcac atccccagcc          2210 aagcctcgaa ctgttgacaa gaccaggag aatccaccca tgggcgccca ccaggttctt           2270 atggatgcaa gcaggagaag ctcaacaccc tgcctcttgc aagacaagg aagcctcacc           2330 tggcttgac ctgccatccg ttgctgaggc cactggcttc catcctaaga atgaggtgca           2390 acaagacccc attctcacag aacctcaaag acttggttcc aggctctcca gagaccatac          2450 ccaactcatg tgcatgtgcc gttttttgctt caagctcagt agcaggacct gccccgagcc         2510 ccctgctcct tgcccctctg tgaggagtta cggagagggc tttgtctcta gagcagaaga         2570
```

-continued

```
gaatgatggg acggcctgat gctgtcatgc tctccactgc acctgtggca gcctcctgag    2630
agccaccaag atctgggatg aaggccacac cagccatgtc tgctgaaggg ccccagactg    2690
agatgactcc ggcctccaca gttagatgtt tatggtgcca gaggtctata ttaaggtagc    2750
tgtctgttgc taggcagccg tttgcacaaa tcttggacat aaatccaact tgaagatcaa    2810
aa                                                                   2812
```

<210> SEQ ID NO 2
<211> LENGTH: 647
<212> TYPE: PRT
<213> ORGANISM: Mus musculus

<400> SEQUENCE: 2

```
Met Glu Gly Arg Gly Pro Tyr Arg Ile Tyr Asp Pro Gly Gly Ser Thr
 1               5                  10                  15

Pro Leu Gly Glu Val Ser Ala Ala Phe Glu Arg Leu Val Glu Glu Asn
            20                  25                  30

Thr Arg Leu Lys Gly Lys Met Gln Gly Ile Lys Met Leu Gly Glu Leu
        35                  40                  45

Leu Glu Glu Ser Gln Met Glu Ala Ser Arg Leu Arg Gln Lys Ala Glu
    50                  55                  60

Glu Leu Val Lys Asp Ser Glu Leu Ser Pro Pro Thr Ser Ala Pro Ser
65                  70                  75                  80

Leu Val Ser Phe Asp Asp Leu Ala Glu Leu Thr Gly Gln Asp Thr Lys
                85                  90                  95

Val Gln Val His Pro Ala Thr Ser Thr Ala Ala Thr Thr Ala Thr
            100                 105                 110

Ala Thr Thr Gly Asn Ser Met Glu Lys Pro Glu Pro Ala Ser Lys Ser
        115                 120                 125

Pro Ser Asn Gly Ala Ser Ser Asp Phe Glu Val Val Pro Thr Glu Glu
    130                 135                 140

Gln Asn Ser Pro Glu Thr Gly Ser His Pro Thr Asn Met Met Asp Leu
145                 150                 155                 160

Gly Pro Pro Pro Glu Asp Ser Asn Leu Lys Leu His Leu Gln Arg
                165                 170                 175

Leu Glu Thr Thr Leu Ser Val Cys Ala Glu Glu Pro Asp His Ser Gln
            180                 185                 190

Leu Phe Thr His Leu Gly Arg Met Ala Leu Glu Phe Asn Arg Leu Ala
        195                 200                 205

Ser Lys Val His Lys Asn Glu Gln Arg Thr Ser Ile Leu Gln Thr Leu
    210                 215                 220

Cys Glu Gln Leu Arg Gln Glu Asn Glu Ala Leu Lys Ala Lys Leu Asp
225                 230                 235                 240

Lys Gly Leu Glu Gln Arg Asp Leu Ala Ala Glu Arg Leu Arg Glu Glu
                245                 250                 255

Asn Thr Glu Leu Lys Lys Leu Leu Met Asn Ser Ser Cys Lys Glu Gly
            260                 265                 270

Leu Cys Gly Gln Pro Ser Ser Pro Lys Pro Glu Gly Ala Gly Lys Lys
        275                 280                 285

Gly Val Ala Gly Gln Gln Ala Ser Val Met Ala Ser Lys Val Pro
    290                 295                 300

Glu Ala Gly Ala Phe Gly Ala Ala Glu Lys Lys Val Lys Leu Leu Glu
305                 310                 315                 320

Gln Gln Arg Met Glu Leu Leu Glu Val Asn Lys Gln Trp Asp Gln His
```

```
                    325                 330                 335
Phe Arg Ser Met Lys Gln Gln Tyr Glu Gln Lys Ile Thr Glu Leu Arg
                340                 345                 350
Gln Lys Leu Val Asp Leu Gln Lys Gln Val Thr Glu Leu Glu Ala Glu
            355                 360                 365
Arg Glu Gln Lys Gln Arg Asp Phe Asp Arg Lys Leu Leu Leu Ala Lys
        370                 375                 380
Ser Lys Ile Glu Met Glu Glu Thr Asp Lys Glu Gln Leu Thr Ala Glu
385                 390                 395                 400
Ala Lys Glu Leu Arg Gln Lys Val Arg Tyr Leu Gln Asp Gln Leu Ser
                405                 410                 415
Pro Leu Thr Arg Gln Arg Glu Tyr Gln Glu Lys Glu Ile Gln Arg Leu
                420                 425                 430
Asn Lys Ala Leu Glu Glu Ala Leu Ser Ile Gln Ala Ser Pro Ser Ser
            435                 440                 445
Pro Pro Ala Ala Phe Gly Ser Pro Glu Gly Val Gly Gly His Leu Arg
        450                 455                 460
Lys Gln Glu Leu Val Thr Gln Asn Glu Leu Leu Lys Gln Gln Val Lys
465                 470                 475                 480
Ile Phe Glu Glu Asp Phe Gln Arg Glu Arg Ser Asp Arg Glu Arg Met
                485                 490                 495
Asn Glu Glu Lys Glu Glu Leu Lys Lys Gln Val Glu Lys Leu Gln Ala
                500                 505                 510
Gln Val Thr Leu Thr Asn Ala Gln Leu Lys Thr Leu Lys Glu Glu Glu
            515                 520                 525
Lys Ala Lys Glu Ala Leu Lys Gln Gln Lys Arg Lys Ala Lys Ala Ser
        530                 535                 540
Gly Glu Arg Tyr His Met Glu Pro His Pro Glu His Val Cys Gly Ala
545                 550                 555                 560
Tyr Pro Tyr Ala Tyr Pro Pro Met Pro Ala Met Val Pro His His Ala
                565                 570                 575
Tyr Lys Asp Trp Ser Gln Ile Arg Tyr Pro Pro Pro Val Pro Met
                580                 585                 590
Glu His Pro Pro His Pro Asn Ser Arg Leu Phe His Leu Pro Glu
                595                 600                 605
Tyr Thr Trp Arg Pro Pro Cys Ala Gly Ile Arg Asn Gln Ser Ser Gln
        610                 615                 620
Val Met Asp Pro Pro Asp Arg Pro Ala Glu Pro Glu Ser Ala Asp
625                 630                 635                 640
Asn Asp Cys Asp Gly Pro Gln
                645

<210> SEQ ID NO 3
<211> LENGTH: 594
<212> TYPE: PRT
<213> ORGANISM: Mus musculus

<400> SEQUENCE: 3

Met Glu Ala Ser Arg Leu Arg Gln Lys Ala Glu Glu Leu Val Lys Asp
1               5                   10                  15
Ser Glu Leu Ser Pro Pro Thr Ser Ala Pro Ser Leu Val Ser Phe Asp
                20                  25                  30
Asp Leu Ala Glu Leu Thr Gly Gln Asp Thr Lys Val Gln Val His Pro
        35                  40                  45
```

```
Ala Thr Ser Thr Ala Ala Thr Thr Thr Ala Thr Ala Thr Gly Asn
     50                  55                  60

Ser Met Glu Lys Pro Glu Pro Ala Ser Lys Ser Pro Ser Asn Gly Ala
 65                  70                  75                  80

Ser Ser Asp Phe Glu Val Val Pro Thr Glu Glu Gln Asn Ser Pro Glu
                 85                  90                  95

Thr Gly Ser His Pro Thr Asn Met Met Asp Leu Gly Pro Pro Pro Pro
                100                 105                 110

Glu Asp Ser Asn Leu Lys Leu His Leu Gln Arg Leu Glu Thr Thr Leu
            115                 120                 125

Ser Val Cys Ala Glu Glu Pro Asp His Ser Gln Leu Phe Thr His Leu
        130                 135                 140

Gly Arg Met Ala Leu Glu Phe Asn Arg Leu Ala Ser Lys Val His Lys
145                 150                 155                 160

Asn Glu Gln Arg Thr Ser Ile Leu Gln Thr Leu Cys Glu Gln Leu Arg
                165                 170                 175

Gln Glu Asn Glu Ala Leu Lys Ala Lys Leu Asp Lys Gly Leu Glu Gln
            180                 185                 190

Arg Asp Leu Ala Ala Glu Arg Leu Arg Glu Glu Asn Thr Glu Leu Lys
        195                 200                 205

Lys Leu Leu Met Asn Ser Ser Cys Lys Glu Gly Leu Cys Gly Gln Pro
210                 215                 220

Ser Ser Pro Lys Pro Glu Gly Ala Gly Lys Lys Gly Val Ala Gly Gln
225                 230                 235                 240

Gln Gln Ala Ser Val Met Ala Ser Lys Val Pro Glu Ala Gly Ala Phe
                245                 250                 255

Gly Ala Ala Glu Lys Lys Val Lys Leu Leu Glu Gln Gln Arg Met Glu
            260                 265                 270

Leu Leu Glu Val Asn Lys Gln Trp Asp Gln His Phe Arg Ser Met Lys
        275                 280                 285

Gln Gln Tyr Glu Gln Lys Ile Thr Glu Leu Arg Gln Lys Leu Val Asp
        290                 295                 300

Leu Gln Lys Gln Val Thr Glu Leu Glu Ala Arg Glu Gln Lys Gln
305                 310                 315                 320

Arg Asp Phe Asp Arg Lys Leu Leu Leu Ala Lys Ser Lys Ile Glu Met
                325                 330                 335

Glu Glu Thr Asp Lys Glu Gln Leu Thr Ala Glu Ala Lys Glu Leu Arg
            340                 345                 350

Gln Lys Val Arg Tyr Leu Gln Asp Gln Leu Ser Pro Leu Thr Arg Gln
        355                 360                 365

Arg Glu Tyr Gln Glu Lys Glu Ile Gln Arg Leu Asn Lys Ala Leu Glu
    370                 375                 380

Glu Ala Leu Ser Ile Gln Ala Ser Pro Ser Ser Pro Ala Ala Phe
385                 390                 395                 400

Gly Ser Pro Glu Gly Val Gly Gly His Leu Arg Lys Gln Glu Leu Val
                405                 410                 415

Thr Gln Asn Glu Leu Leu Lys Gln Gln Val Lys Ile Phe Glu Glu Asp
            420                 425                 430

Phe Gln Arg Glu Arg Ser Asp Arg Glu Arg Met Asn Glu Glu Lys Glu
        435                 440                 445

Glu Leu Lys Lys Gln Val Glu Lys Leu Gln Ala Gln Val Thr Leu Thr
    450                 455                 460

Asn Ala Gln Leu Lys Thr Leu Lys Glu Glu Glu Lys Ala Lys Glu Ala
```

-continued

```
                465                 470                 475                 480
Leu Lys Gln Gln Lys Arg Lys Ala Lys Ala Ser Gly Glu Arg Tyr His
                    485                 490                 495
Met Glu Pro His Pro Glu His Val Cys Gly Ala Tyr Pro Tyr Ala Tyr
                500                 505                 510
Pro Pro Met Pro Ala Met Val Pro His His Ala Tyr Lys Asp Trp Ser
            515                 520                 525
Gln Ile Arg Tyr Pro Pro Pro Val Pro Met Glu His Pro Pro Pro
        530                 535                 540
His Pro Asn Ser Arg Leu Phe His Leu Pro Glu Tyr Thr Trp Arg Pro
545                 550                 555                 560
Pro Cys Ala Gly Ile Arg Asn Gln Ser Ser Gln Val Met Asp Pro Pro
                565                 570                 575
Pro Asp Arg Pro Ala Glu Pro Glu Ser Ala Asp Asn Asp Cys Asp Gly
            580                 585                 590
Pro Gln

<210> SEQ ID NO 4
<211> LENGTH: 19
<212> TYPE: PRT
<213> ORGANISM: Artificial Sequence
<220> FEATURE:
<223> OTHER INFORMATION: Description of Artificial Sequence: consensus
      amino acid sequence 1 (WO99/57133)
<220> FEATURE:
<221> NAME/KEY: misc_feature
<222> LOCATION: (2)..(4)
<223> OTHER INFORMATION: Xaa is any amino acid
<220> FEATURE:
<221> NAME/KEY: misc_feature
<222> LOCATION: (8)..(8)
<223> OTHER INFORMATION: Xaa is any amino acid
<220> FEATURE:
<221> NAME/KEY: misc_feature
<222> LOCATION: (12)..(13)
<223> OTHER INFORMATION: Xaa is any amino acid
<220> FEATURE:
<221> NAME/KEY: misc_feature
<222> LOCATION: (17)..(18)
<223> OTHER INFORMATION: Xaa is any amino acid

<400> SEQUENCE: 4

Glu Xaa Xaa Xaa Lys Glu Ile Xaa Arg Leu Asn Xaa Xaa Leu Glu Glu
  1               5                  10                  15
Xaa Xaa Ser

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: consensus
      amino acid sequence 2 (WO99/57133)
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (5)..(10)
<223> OTHER INFORMATION: Xaa is any amino acid
<220> FEATURE:
<221> NAME/KEY: misc_feature
<222> LOCATION: (13)..(14)
<223> OTHER INFORMATION: Xaa is any amino acid
<220> FEATURE:
<221> NAME/KEY: misc_feature
```

```
<222> LOCATION: (17)..(17)
<223> OTHER INFORMATION: Xaa is any amino acid

<400> SEQUENCE: 5

Leu Xaa Gln Gln Xaa Xaa Xaa Xaa Xaa Xaa Asp Phe Xaa Xaa Glu Arg
 1               5                  10                  15

Xaa Asp Arg Glu Arg
            20

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: forward
      primer: amplification of murine ABIN cDNA

<400> SEQUENCE: 6
cgggatccgc catgggtgcg ccggtgcc                                          28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: reverse
      primer: amplification of murine ABIN cDNA

<400> SEQUENCE: 7
ccccaagctt aaatgaccca ctgcagcc                                          28

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      labelled DNA
      probe

<400> SEQUENCE: 8
agctagaggg gasctttccg agagg                                             25
```